US012329546B2

United States Patent
Chung et al.

(10) Patent No.: US 12,329,546 B2
(45) Date of Patent: Jun. 17, 2025

(54) STRESS PREDICTION BASED ON NEURAL NETWORK

(71) Applicant: University of Pittsburgh—Of the Commonwealth System of Higher Education, Pittsburgh, PA (US)

(72) Inventors: Timothy K. Chung, Pittsburgh, PA (US); David A. Vorp, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 46 days.

(21) Appl. No.: 17/769,327

(22) PCT Filed: Oct. 14, 2020

(86) PCT No.: PCT/US2020/055511
§ 371 (c)(1),
(2) Date: Apr. 14, 2022

(87) PCT Pub. No.: WO2021/076575
PCT Pub. Date: Apr. 22, 2021

(65) Prior Publication Data
US 2024/0303804 A1    Sep. 12, 2024

Related U.S. Application Data

(60) Provisional application No. 62/915,565, filed on Oct. 15, 2019.

(51) Int. Cl.
*A61B 5/00* (2006.01)
*G06T 7/00* (2017.01)
(Continued)

(52) U.S. Cl.
CPC .......... *A61B 5/7267* (2013.01); *G06T 7/0012* (2013.01); *G06T 7/13* (2017.01);
(Continued)

(58) Field of Classification Search
CPC .......... A61B 6/032; A61B 5/055; A61B 6/025; A61B 5/0035; A61B 5/0059; A61B 6/06;
(Continued)

(56) References Cited

U.S. PATENT DOCUMENTS

| 2002/0137014 A1 | 9/2002 | Anderson et al. |
| 2008/0253638 A1 | 10/2008 | Binkley et al. |
| 2017/0200067 A1* | 7/2017 | Zhou .................. G06V 30/194 |

OTHER PUBLICATIONS

"Semiautomatic vessel wall detection and quantification of wall thickness in computed tomography images of human abdominal aortic aneurysms" Med Phys., vol. 37, No. 2, pp. 638-648. (Year: 2010).*

(Continued)

*Primary Examiner* — Ajibola A Akinyemi
(74) *Attorney, Agent, or Firm* — Foley & Lardner LLP

(57) ABSTRACT

Disclosed herein are related to a system, a method, and a non-transitory computer readable medium for simulating, predicting, or estimating, based on machine learning neural networks, wall stress of a body part. In one approach, a first neural network automatically detects features in multiple images of a body part. For example, the first neural network may detect, for each image, a lumen and a wall of an aorta. According to the detected features, a second neural network may simulate, estimate, or predict wall stress of the body part in response to pressure applied to the body part. For example, a model generator can generate a three-dimensional model of the body part according to the detected features in the multiple images, and the second neural network can simulate, estimate, or predict wall stress of the body part according to the three-dimensional model.

19 Claims, 17 Drawing Sheets

(51) Int. Cl.
  *G06T 7/13* (2017.01)
  *G06T 7/60* (2017.01)
  *G06T 17/00* (2006.01)
  *G06V 10/26* (2022.01)
  *G06V 10/75* (2022.01)
  *G06V 20/64* (2022.01)

(52) U.S. Cl.
  CPC ............... *G06T 7/60* (2013.01); *G06T 17/00* (2013.01); *G06V 10/26* (2022.01); *G06V 10/754* (2022.01); *G06V 20/653* (2022.01); *G06T 2207/20084* (2013.01); *G06T 2207/30048* (2013.01); *G06T 2207/30101* (2013.01)

(58) Field of Classification Search
  CPC ... A61B 6/4014; A61B 6/4085; A61B 6/4435; A61B 6/4452; A61B 6/488; A61B 2034/2051; A61B 2034/107; A61B 34/20; A61B 2090/378; A61B 2090/3908
  USPC ........................................................ 382/128
  See application file for complete search history.

(56) References Cited

OTHER PUBLICATIONS

International Search Report and Written Opinion for PCT Appl. No. PCT/US2020/055511, mailed Jan. 26, 2021.

Kissas et al., "Machine learning in cardiovascular flows modeling: Predicting arterial blood pressure from non-invasive 4D flow MRI data using physics-informed neural networks" Computer Methods in Applied Mechanics and Engineering, Sep. 17, 2019.

Shen et al., "Total body skeletal muscle and adipose tissue volumes: estimation from a single abdominal cross-sectional image" *Journal of applied physiology*, Aug. 13, 2004.

Shum et al., "Semiautomatic vessel wall detection and quantification of wall thickness in computed tomography images of human abdominal aortic aneurysms" Med Phys., vol. 37, No. 2, pp. 638-648 (2010).

International Preliminary Report on Patentabilty for PCT Appl. No. PCT/US2020/055511, mailed Apr. 28, 2022.

* cited by examiner

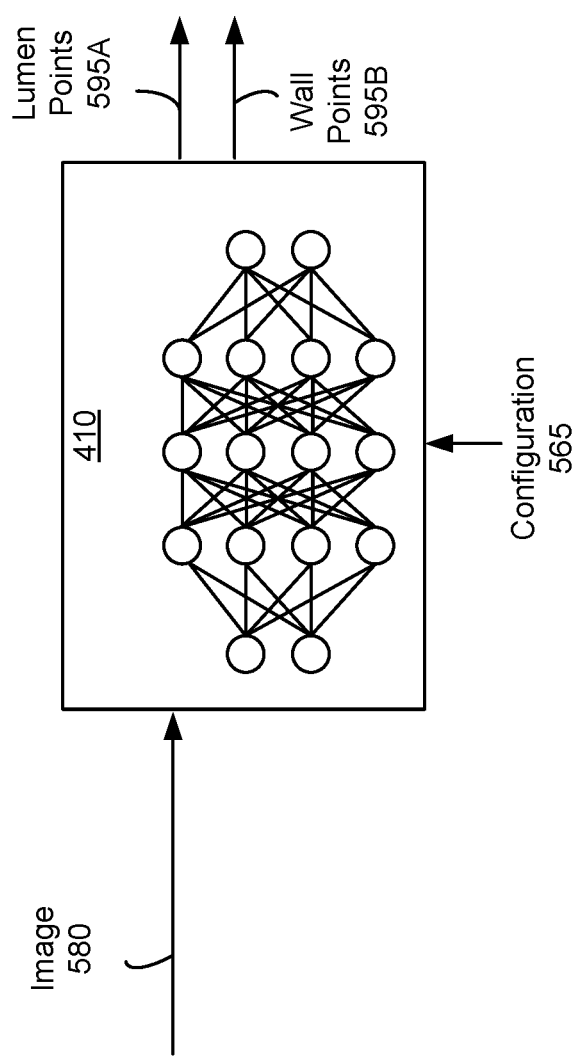

STRESS PREDICTION BASED ON NEURAL NETWORK

CROSS-REFERENCE TO RELATED APPLICATIONS

This is a National Stage Application, filed under 35. U.S.C. § 371, of PCT Application No. PCT/US2020/055511, filed on Oct. 14, 2020, which claims the benefit of priority of U.S. Provisional Application No. 62/915,565, filed on Oct. 15, 2019, the contents of which are incorporated herein in their entirety.

STATEMENT OF GOVERNMENT SUPPORT

This invention was made with government support under #HL079313 awarded by the National Institutes of Health. The government has certain rights in the invention.

FIELD OF DISCLOSURE

The present disclosure is generally related to a simulator for a body part, including but not limited to a simulator for predicting wall stress of a body part and implemented based on machine learning.

BACKGROUND

An abdominal aortic aneurysm (AAA) is a blood-filled bulge or ballooning in a part of an aorta. The AAA can cause rupture in an aorta, and may cause excessive blood loss. Wall stress of the aorta due to pressure applied can be simulated to analyze or predict the risk of rupture in an aorta. For example, a three-dimensional model of the aorta can be generated through a manual process, and simulation data is prepared through a convoluted and manual process for simulation using software like Abaqus. However, such a process of manually generating the three-dimensional model and simulation data can be laborious and time consuming. Moreover, the process of computing the wall stress for various points of the three-dimensional model can be time consuming and computationally exhaustive.

SUMMARY

In one aspect, encompassed by the disclosure is a system comprising: (a) a first neural network configured to: (i) detect, from a first image of a first cross section of a body part and its surrounding body part, a first outer boundary of the first cross section of the body part and a first inner boundary of the first cross section of the body part, and (ii) detect, from a second image of a second cross section of the body part and the surrounding body part, a second outer boundary of the second cross section of the body part and a second inner boundary of the second cross section of the body part; and (b) a second neural network configured to: (i) predict wall stress of the body part, according to geometry information derived from the first outer boundary, the first inner boundary, the second outer boundary and the second inner boundary.

In another aspect, encompassed is a system further comprising a model generator coupled between the first neural network and the second neural network, the model generator configured to generate a three dimensional model of the body part according to the first outer boundary, the first inner boundary, the second outer boundary and the second inner boundary, the geometry information comprising the three dimensional model, wherein the second neural network is configured to predict the wall stress of the body part according to the three dimensional model of the body part.

In yet another aspect, encompassed is a system wherein the model generator is configured to generate the three dimensional model by: connecting points on the first outer boundary of the first cross section of the body part and points on the second outer boundary of the second cross section of the body part, and connecting points on the first inner boundary of the first cross section of the body part and points on the second inner boundary of the second cross section of the body part.

In one embodiment of the disclosure, the body part has a tubular structure. In one embodiment, the body part can be an artery, the first outer boundary and the second outer boundary corresponding to a wall of the artery, and the first inner boundary and the second inner boundary corresponding to a lumen of the artery. In one embodiments, the body part includes other types of soft tissues in musculoskeletal systems that rely on boundaries (cortical/cancellous bone, ligaments, tendons and organs).

In yet another aspect, the model generator can be configured to determine a plurality of shape indices from the generated three dimensional model, and provide the plurality of shape indices as input to the second neural network to predict the wall stress of the body part.

The disclosure also encompasses a system wherein the geometry information includes shape indices and location information of the shape indices. For example, the shape indices can include at least one of: a z-height ratio, a distance to a centroid, regional mapping indicating relative relationship between anterior/posterior/lateral views or the standard axes in upright posture (left-right axis, craniocaudal axis and anteroposterior axis), an intraluminal thrombus thickness, a principal curvature of a neighboring node, tortuosity, or a wall to lumen vector, or any localized morphological parameters that can be normalized.

In another embodiment, in a training phase for the second neural network, the second neural network can be configured to: (a) predict the wall stress of the body part in response to varying pressure, dynamic movement or linear or angular force; (b) compare the predicted wall stress with a target wall stress of the body part; and/or (c) update a configuration of the second neural network according to the comparison.

The system of the disclosure can additionally comprise a geometric information generator coupled between the first neural network and the second neural network, the geometric information generator configured to determine the geometry information according to the first outer boundary, the first inner boundary, the second outer boundary, and the second inner boundary, the geometry information comprising a plurality of shape indices.

In another aspect of the system of the disclosure, the second neural network comprises a regression model. The regression model may be any regression model. In yet another aspect, the first neural network comprises a convolutional neural network.

The system of the disclosure can further comprise a risk determiner configured to determine a risk of an aneurysm according to the predicted wall stress of the body part.

In one aspect of the disclosure, during a training phase of the first neural network, the first neural network is configured to: (a) receive, as part of training data, a plurality of images each comprising a corresponding cross section of the body part and the surrounding body part; and (b) receive, as part of the training data, for each of the plurality of images, an outer boundary of the corresponding cross section of the body part, and an inner boundary of the corresponding cross section of the body part Also encompassed by the disclosure is a method, optionally using the system described herein. The method comprises, for example, (a) detecting, by a first neural network, from a first image of a first cross section of a body part of a subject and its surrounding body part, a first outer boundary of the first cross section of the body part and a first inner boundary of the first cross section of the body part; (b) detecting, by the first neural network, from a second image of a second cross section of the body part and the surrounding body part, a second outer boundary of the second cross section of the body part and a second inner boundary of the second cross section of the body part; and (c) predicting, by a second neural network, wall stress of the body part of the subject, according to geometry information derived from the first outer boundary, the first inner boundary, the second outer boundary and the second inner boundary.

In one aspect of the method, the method the method is used to evaluate in the subject a risk of an aneurysm, which can be for example, an abdominal aortic aneurysm, ascending thoracic aneurysm, a ventricular aneurysm, or a brain aneurysm.

In another aspect of the method, the subject's body part has a tubular structure or rigid structure of a musculoskeletal system. Examples of body parts that can be evaluated using the method and/or system of the disclosure include, but are not limited to, aorta, artery, ureter, intestine, cortical/cancellous bones, ligaments, tendons and heart.

In yet another aspect of the method of the disclosure, the method can be completed in a time period of less than about 15 minutes. In another aspect, the method can be completed in a time period of less than about 14 minutes, less than about 13 minutes, less than about 12 minutes, less than about 11 minutes, less than about 10 minutes, less than about 9 minutes, less than about 8 minutes, less than about 7 minutes, less than about 6 minutes, or about 5 minutes or less. Optionally, the method can be completed in a time period of less than about 4 minutes, less than about 3 minutes, less than about 2 minutes, less than about 1 minute, less than about 45 sec, less than about 30 sec, less than about 20 sec, less than about 15 sec, or about 10 see or less.

Finally, in the method of the disclosure the subject can be a member of a patient population at risk for an aneurysm.

In still another aspect, encompassed by the disclosure is a system comprising: (a) a first neural network configured to detect, from a first image of a first cross section of a body part and its surrounding body part, a first outer boundary of the first cross section of the body part and a first inner boundary of the first cross section of the body part; and (b) a second neural network configured to predict wall stress of the body part, according to geometry information derived from the first outer boundary, and the first inner boundary.

Both the foregoing summary and the following description of the drawings and detailed description are exemplary and explanatory. They are intended to provide further details of the invention, but are not to be construed as limiting. Other objects, advantages, and novel features will be readily apparent to those skilled in the art from the following detailed description of the invention.

BRIEF DESCRIPTION OF THE DRAWINGS

The accompanying drawings are not intended to be drawn to scale. Like reference numbers and designations in the various drawings indicate like elements. For purposes of clarity, not every component can be labeled in every drawing.

FIG. 5B is a block diagram of a neural network of a feature extractor in a run time phase, according to an example implementation of the present disclosure.

DETAILED DESCRIPTION

Figure 1:
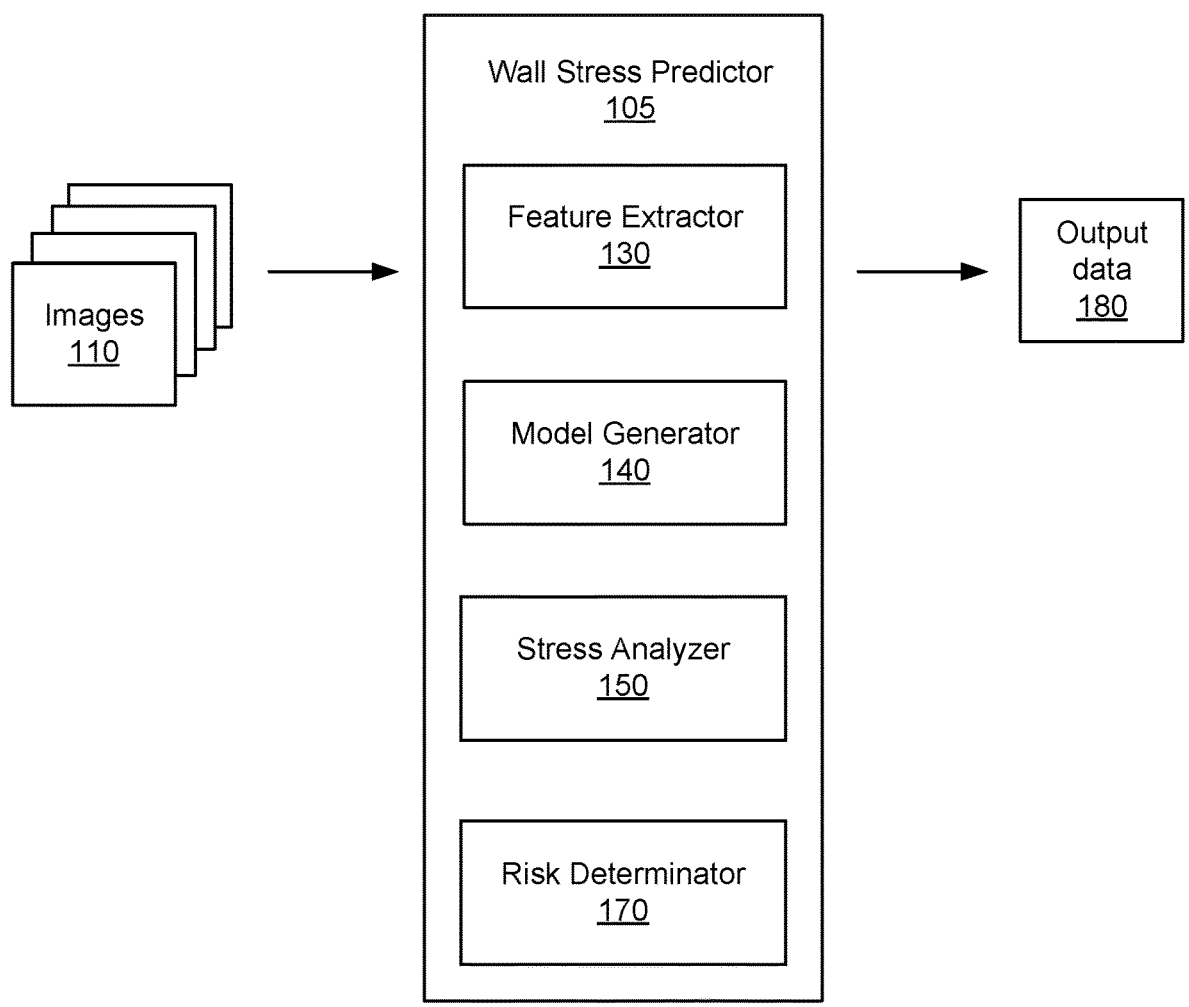
FIG. 1 is a block diagram of a system for predicting wall stress of a body part, according to an example implementation of the present disclosure.

Before turning to the figures, which illustrate certain embodiments in detail, it should be understood that the present disclosure is not limited to the details or methodology set forth in the description or illustrated in the figures. It should also be understood that the terminology used herein is for the purpose of description only and should not be regarded as limiting.

Disclosed herein include embodiments of a system, a method, and a non-transitory computer readable medium for simulating, predicting, or estimating, based on machine learning neural networks, wall stress of a body part. A body part can be any part of a human body having a tubular structure, such as aorta, artery, ureter, intestine, cortical/cancellous bones, ligaments, tendons, heart, etc., and can be characterized by wall stress due to pressure applied to wall portions of the body part. In one approach, a first neural network automatically detects features in multiple images of a body part. Examples of features in an image include points on the outer boundary and the inner boundary of (e.g., wall, lining and/or tissue portions of) the body part in the image. For example, the first neural network may detect, for each image, a lumen and a wall of an aorta. According to the detected features, a second neural network may simulate, estimate, or predict wall stress of the body part in response to pressure applied to the body part. For example, a model generator can generate a three-dimensional model of the body part according to the detected features in the multiple images, and the second neural network can simulate, estimate, or predict wall stress of the body part according to the three-dimensional model.

Advantageously, the disclosed system, method, and non-transitory computer readable medium can improve computational efficiency in simulating wall stress of a body part via neural networks. In one implementation, features in multiple images can be identified through a manual process, and a three dimensional model can be generated according to the manually identified features. Moreover, wall stress of the body part in response to pressure applied can be simulated according to the shape or geometry of the body part indicated by the three dimensional model. However, manually detecting features in the multiple images and simulating wall stress of the body part according to the shape or geometry of the body part indicated by the three dimensional model can be computationally exhaustive and may take a long time (e.g., over 10 hours). By automatically detecting features of a body part in multiple images and/or simulating wall stress of the body part according to the detected features of the body part via one or more machine learning neural networks, computational resources (e.g., processing resources and storage amount) can be conserved, and wall stress of the body part can be simulated, estimated, or predicted in a prompt manner (e.g., less than five minutes). Although some examples disclosed herein are provided with respect to predicting wall stress for AAA, the principle disclosed herein can be applied for any other type of aneurysms (e.g., ventricular aneurysm, brain aneurysm, etc.) or any type of body part having a tubular structure or subject to stress on a wall or lining portion.

FIG. 1 is a block diagram of a system 100 for predicting wall stress of a body part, according to an example implementation of the present disclosure. In some embodiments, the system 100 includes a feature extractor 130, a model generator 140, a stress analyzer 150, and a risk determinator 170. These components may operate together to receive images 110 of a body part and can simulate, predict, or estimate wall stress of the body part due to pressure applied to the body part. In some embodiments, the feature extractor 130, the model generator 140, the stress analyzer 150, the risk determinator 170 or any combination of them is implemented on a hardware, or a combination of software and hardware. For example, the feature extractor 130, the model generator 140, the stress analyzer 150, and the risk determinator 170 can be implemented as software modules executing on one or more processors. For another example, the feature extractor 130, the model generator 140, the stress analyzer 150, and the risk determinator 170 can be implemented as hardware components such as a neural network chip, a field programmable gate logic (FPGA) and/or an application specific integrated circuit (ASIC). In some embodiments, the system 100 includes more, fewer, or different components than shown in FIG. 1.

The feature extractor 130 includes or corresponds to a component that receives images 110 and detects features in the images 110, in one or more embodiments. The images may be cross sectional images including a body part and its surrounding body parts or anatomy. For example, the images may include Digital Imaging and Communications in Medicine (DICOM) images. For example, the images may be different cross sectional images including a part of a human body having a tubular and/or wall-like structure, such as an aorta, artery, ureter, intestine, heart, etc. The feature extractor 130 may detect, for each image, a corresponding set of features. A set of features of an image may include a set of points in the image corresponding to outer boundaries and/or inner boundaries of a body part. Thus, the feature extractor 130 can extract, segregate, or localize the body part from its surrounding body part. The feature extractor 130 may aggregate different sets of points for different images as a point cloud (e.g., an imaging or spatial representation of the body part). In some embodiments, the feature extractor 130 includes a neural network (e.g., convolutional neural network) that can detect features in the images 110 as described below with respect FIGS. 4, 5A, 5B, 6, 10 and 11 below.

The model generator 140 includes or corresponds to a component that generates a three dimensional model according to the detected features in the images, in one or more embodiments In one approach, the model generator 140 generates a three dimensional mesh model of a body part by connecting points of the body part. For example, the model generator 140 generates a mesh model corresponding to a wall, and/or a mesh model corresponding to a lumen. The model generator 140 may synthesize and/or combine the mesh model of the wall and the mesh model of the lumen to generate a mesh model of an aorta (or any body part having a tubular and/or wall-like structure). The model generator 140 may represent the three dimensional model with shape indices and location information of the shape indices. For example, a shape index can include wall centerline and lumen centerline that serve as a reference of base geometry. A shape index for a point in a three dimensional model may describe a wall, a lumen, or a relationship between the wall and the lumen. The shape index for the point may for example indicate or include a z-height ratio (e.g., ratio of a current height of the point along the z axis, to a total height of a corresponding aneurysm), a distance to a centroid, an intraluminal thrombus thickness (e.g., a distance from the point on the wall to a closest point on the lumen), a principal curvature of a neighboring node/point, tortuosity, labelled position that includes whether the point falls on a proximal or distal neck location, aneurysm sac and boundary conditions (e.g., edges of the aneurysm), and/or a wall to lumen vector (e.g., direction and magnitude to closest lumen point using a minimization function), etc., at the point in the three dimensional model. The three dimensional model may be used for predicting wall stress according to shape or geometry of the body part.

The stress analyzer 150 includes or corresponds to a component that simulates, predicts, or estimates wall stress of a body part, in one or more embodiments. In one aspect, the stress analyzer 150 predicts the wall stress of the body part according to geometry information of the body part indicating morphological aspects of the body part. In some embodiments, geometry information may be derived (e.g., directly) from the detected features in the feature extractor 130. In these embodiments, the model generator 140 may be bypassed or omitted. Additionally or alternatively, in some embodiments, geometry information may be shape indices and location information of the shape indices from the model generator 140. The stress analyzer 150 may predict wall stresses according to the geometry information, and generate stress data indicating wall stress at various points of the three dimensional model. In some embodiments, the stress analyzer 150 includes a neural network (e.g., convolutional neural network or a regression model) that predicts wall stress of a body part according to geometry information as described below with respect FIGS. 4, 8A, 8B, 10 and 11 below.

The risk determinator 170 includes or corresponds to a component that receives stress data from the stress analyzer 150 and automatically performs risk analysis, in one or more embodiments. In one example, the risk determinator 170 compares, for each point of a three dimensional model of a body part, wall stress with a predetermined threshold (e.g., 15 N/cm$^2$ for failure strength). In some embodiments, the risk determinator 170 may calculate or determine the wall stress as a rupture potential index for instance. Wall stress may be described or indicated via any unit for stress/pressure, such as Newton per unit area, pascal, etc. The threshold may be set or adjustable by a user through a user interface. The risk determinator 170 may generate an image of the three dimensional model of a body part, where one or more points having wall stress exceeding the predetermined threshold are highlighted or indicated in a different color than other points of the three dimensional model for instance. The risk determinator 170 may provide the image as output data 180 to a display device, for example. Hence, a user operating the wall stress predictor 105 or viewing its results can easily identify any points of the three dimensional model of the body part at risk of rupture.

Figure 2A:
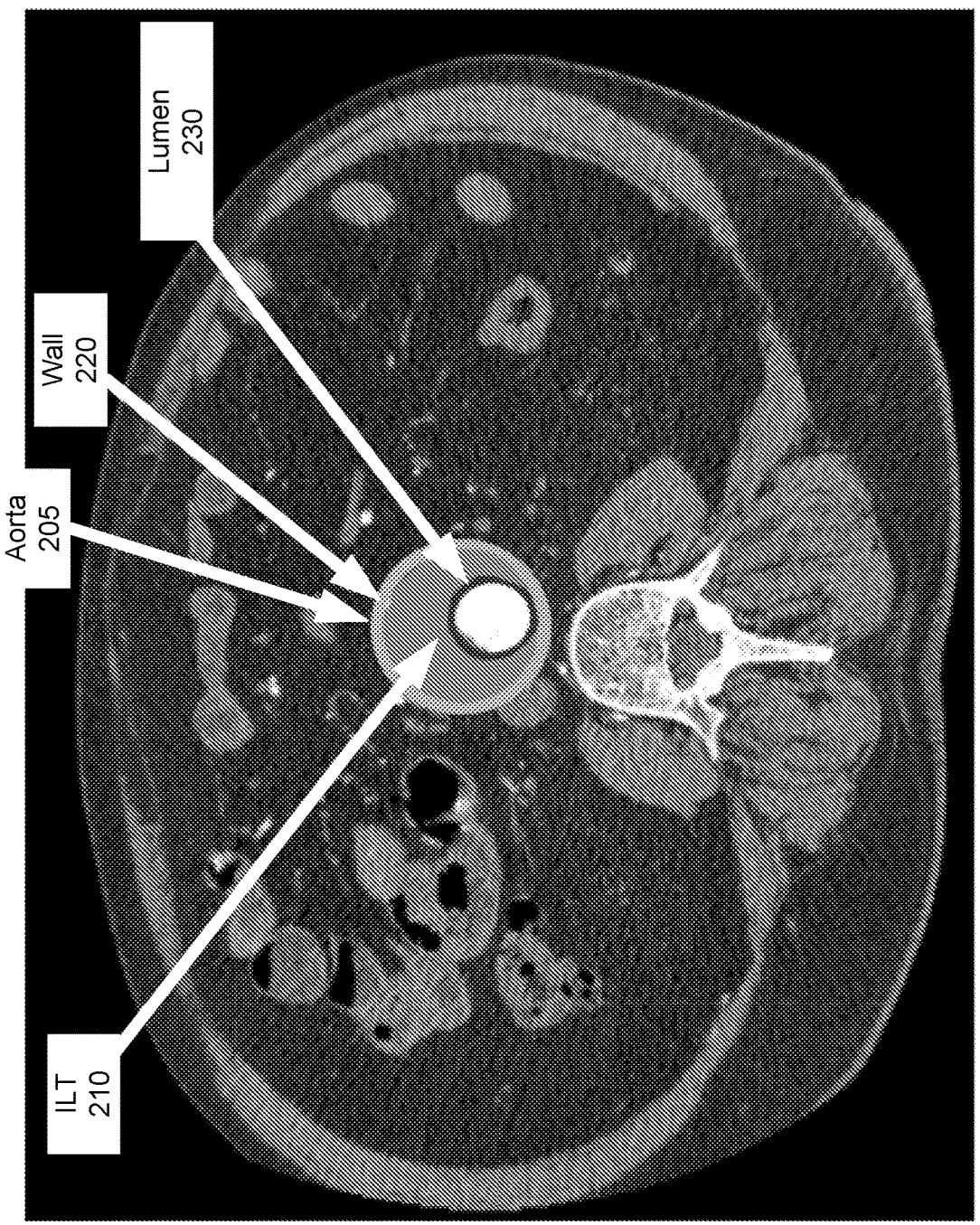
FIG. 2A is an example cross sectional image of an aorta, according to an example implementation of the present disclosure.

FIG. 2A is an example cross sectional image 200 of an aorta 205, according to an example implementation of the present disclosure. In one aspect, the image 200 captures a cross section of a human body portion with an aorta 205 and its surrounding body parts. The aorta 205 includes or is characterized by a wall 220, a lumen 230 and an intraluminal thrombus (ILT) 210. The wall 220 defines or corresponds to an outer boundary of the aorta 205 and the lumen 230 defines or corresponds to an inner boundary of the aorta 205. Between the aorta 205 and the lumen 230 is a region that may be filled with ILT 210. Hence, the aorta 205 has a tubular structure, where blood may flow through the space within the lumen 230. In one approach, the feature extractor 130 may automatically detect, for different cross-sectional images, the lumen 230, the ILT 210, and/or the wall 220 of the aorta 205.

Figure 2B:
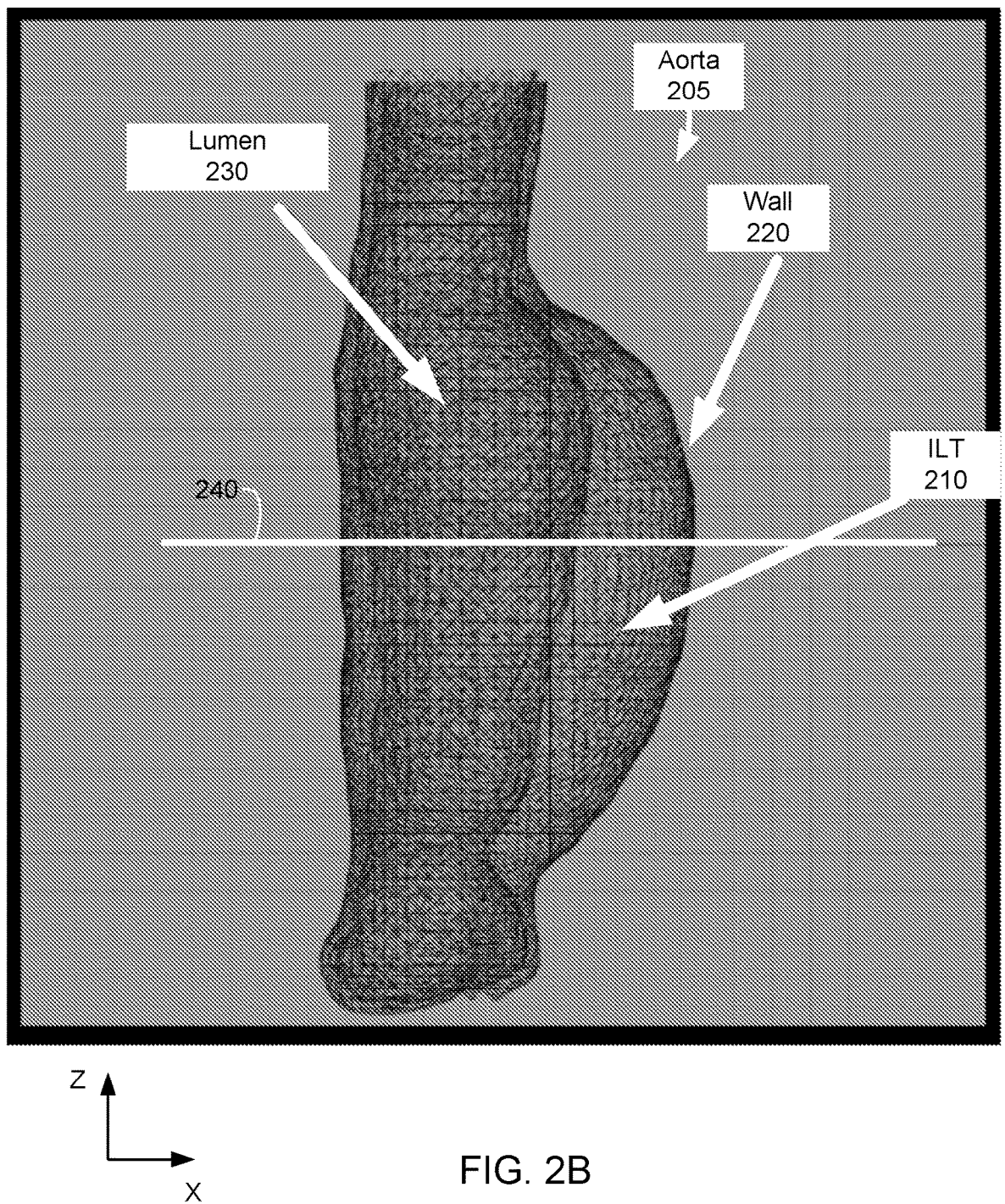
FIG. 2B is an example image of an aorta with abdominal aortic aneurysm, according to an example implementation of the present disclosure.

FIG. 2B is an example image 260 of the aorta 205 with AAA, according to an example implementation of the present disclosure. In one example, the model generator 140 generates a three dimensional model of the aorta 205 according to the lumen 230, the ILT 210, and the wall 220 of the aorta 205 detected at various cross sectional images capturing different cross sections of a body portion along a z direction. For example, the lumen 230, the ILT 210, and the wall 220 of the aorta 205 on a horizontal plane 240 are detected from the cross-sectional image 200. By connecting the lumen 230, the ILT 210, and the wall 220 of the aorta 205 detected in different cross sectional images along the z direction, a three dimensional model of the aorta 205 can be constructed in some embodiments.

Figure 3:
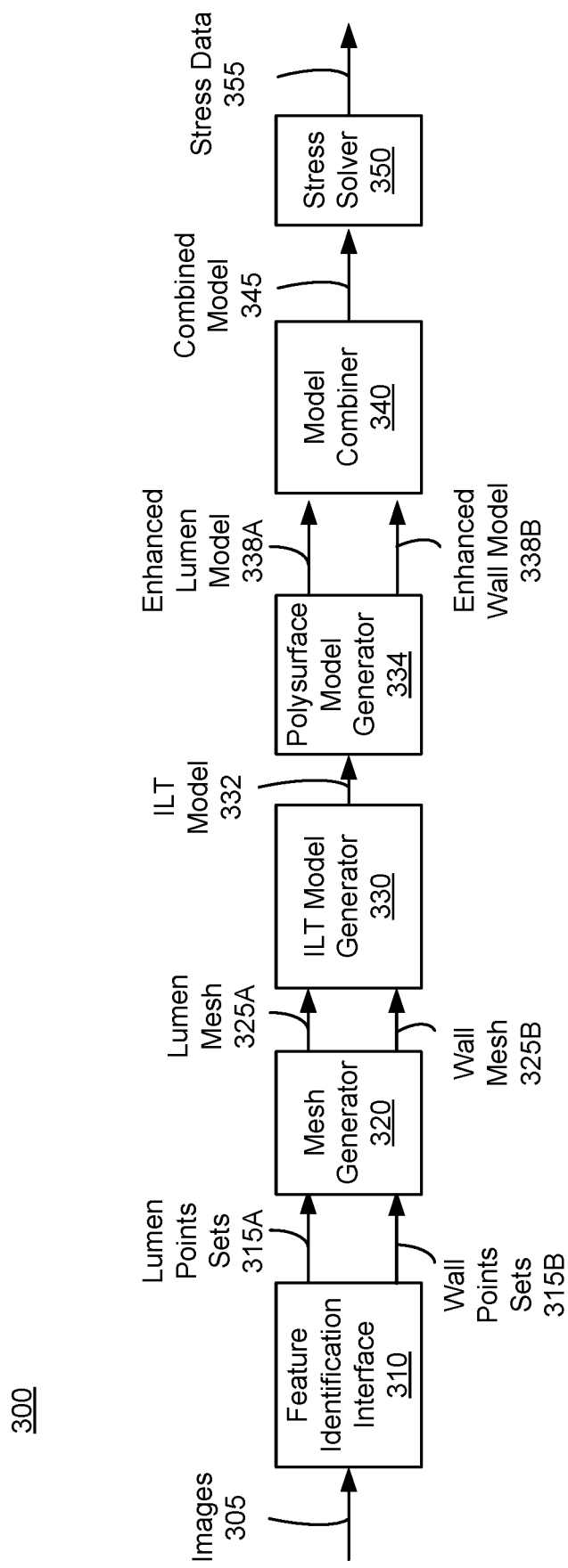
FIG. 3 is a block diagram of a system for computing wall stress of a body part, according to an example implementation of the present disclosure.

FIG. 3 is a block diagram of a system 300 for computing wall stress of a body part, according to an example implementation of the present disclosure. In some embodiments, the system 300 includes a feature identification interface 310, a mesh generator 320, an ILT model generator 330 to, for example, perform Boolean operations (e.g., Boolean differences), a polysurface model generator 334, a model combiner 340, and a stress solver 350. These components may operate together to detect features in images 305, and generate stress data 355 indicating wall stress of a body part (e.g., aorta). The images 305 may be cross sectional images of a body including a body part and its surrounding body parts (or anatomy). In some embodiments, the system 300 is separate from the system 100 of FIG. 1. In some embodiments, the system 300 is integrated as part of the system 100 of FIG. 1.

The feature identification interface 310 includes or corresponds to a component that generates a user interface allowing a user of the system 300 to indicate or select a set of points in an image, in some embodiments. In one example, the feature identification interface 310, through the user interface, presents a cross sectional image of a body, and receives user commands indicating points corresponding to an outer boundary and an inner boundary of a body part. For example, the feature identification interface 310 can receive, from a user, coordinates of a set of lumen points and a set of wall points for an image. The feature identification interface 310 may receive additional sets of lumen points and sets of wall points for different cross sectional images of the body, for example, along the z direction. Hence, the feature identification interface 310 can receive multiple sets of lumen points 315A and multiple sets of wall points 315B of a body part defined or selected by the user. In one aspect, sets of lumen points and sets of wall points can be stacked along the z direction. Hence, each point may be identified by a corresponding three-dimensional Cartesian coordinate (x, y, z).

The mesh generator 320 includes or corresponds to a component that generates mesh models 325A, 325B according to the sets of lumen points 315A and the sets of wall points 315B, in some embodiments. In one example, the mesh generator 320 connects the sets of lumen points 315A to generate a lumen mesh model 325A, and connects the sets of wall points 315B to generate a wall mesh model 325B. For example, the mesh generator 320 may connect each set of lumen points 315A in a corresponding cross sectional image with an adjacent set of lumen points 315A in a subsequent cross sectional image. Similarly, the mesh generator 320 may connect each set of wall points 315B for a corresponding cross sectional image with an adjacent set of wall points 315B for a subsequent cross sectional image.

In some embodiments, the ILT model generator 330 obtains a mesh model of an ILT according to the mesh models 325A, 325B. In one approach, the ILT model generator 330 obtains a Boolean difference between the lumen mesh model 325A and the wall mesh model 325B, which corresponds to the ILT model 332. In one aspect, the ILT model generator 330 converts or maps each point in a Cartesian coordinate (x, y, z) into a distance map with respect to a corresponding centroid. The ILT model generator 330 may determine, for each image, a corresponding centroid point. A centroid point may be a center of a cross section of a wall in the image. The ILT model generator 330 may determine different centroid points for different cross sectional images along the z direction. Hence, the centroid points can be connected to form a center line or curve. The ILT model generator 330 may determine, for each point of a set of points in an image, a corresponding distance from a centroid point in the image. The set of lumen points 315A and the set of wall points 315B in an image may be mapped according to the same centroid point of the image. Thus, the ILT model generator 330 may determine a difference between a distance of a wall point from a centroid point and a distance of a corresponding lumen point from the centroid point, where the difference corresponds to a thickness of the ILT between the wall point and the lumen point. The ILT model generator 330 may generate the ILT model 332 indicating locations and thicknesses of various points of the ILT.

The polysurface model generator 334 includes or corresponds to a component that generates enhanced models 338A, 338B of the body part according to the ILT model 332, in some embodiments. In one approach, the polysurface model generator 334 generates an enhanced lumen model 338A and an enhanced wall model 338B of the body part having polysurfaces according to the ILT model 332. For example, the polysurface model generator 334 generates polygons or polysurfaces (e.g., triangles) surrounding the ILT, according to locations, topologies and/or depths of various points of the ILT. For example, the polysurface model generator 334 generates the enhanced models 338A, 338B in a .sat file format.

The model combiner 340 includes or corresponds to a component that generates a combined model 345 according to the enhanced lumen model 338A, and the enhanced wall model 338B, in some embodiments. The combined model 345 may include geometry information of the body part indicating morphological aspects of the body part. The geometry information may include shape indices and location information (e.g., Cartesian, Spherical or Cylindrical coordinates) of the shape indices. For example, the shape indices include at least one of: a z-height ratio, a distance to a centroid, an ILT thickness, a principal curvature of a neighboring node, tortuosity, or a wall to lumen vector, etc. Further, the shape indices can be normalized, and applied as a global quantity within a population.

The stress solver 350 includes or corresponds to a component that simulates, estimates, or predicts wall stress of the body part according to the combined model 345 from the model combiner 340. The stress solver 350 may be implemented as simulation solver or program (e.g., Abaqus software for finite element analysis and computer-aided engineering, from Abaqus, Inc.). In one aspect, the stress solver 350 may also obtain and/or use material information indicating hardness or tension of different components (e.g., ILT) of the body part. In one approach, the stress solver 350 determines, for each point or for each surface, corresponding wall stress in response to pressure applied due to a flow, presence and/or accumulation of fluid (e.g., blood) in the body part. For example, wall stress in response to pressure applied the body part with a thickness can be computed according to the following equation (Law of Laplace): $WS \cong (P \times R)/Th$, where WS is wall stress, P is pressure applied, R is a radius of lumen, and Th is a thickness of wall, for example, for a thin-walled cylinder. The stress solver 350 may generate and output the stress data 355 indicating, for each point or for each surface, corresponding wall stress.

In one example, the process of generating stress data 355 according to images 305 by the system 300 as shown in FIG. 3 may be computationally inefficient and may take a long time (e.g., over 10 hours). For example, manually detecting features in the multiple images 305 through the user interface can be a laborious process and may take many hours. Moreover, computing wall stress of the body part for each point or each surface can be computationally exhaustive and may take a long time (e.g., over 5-6 hours).

Figure 4:
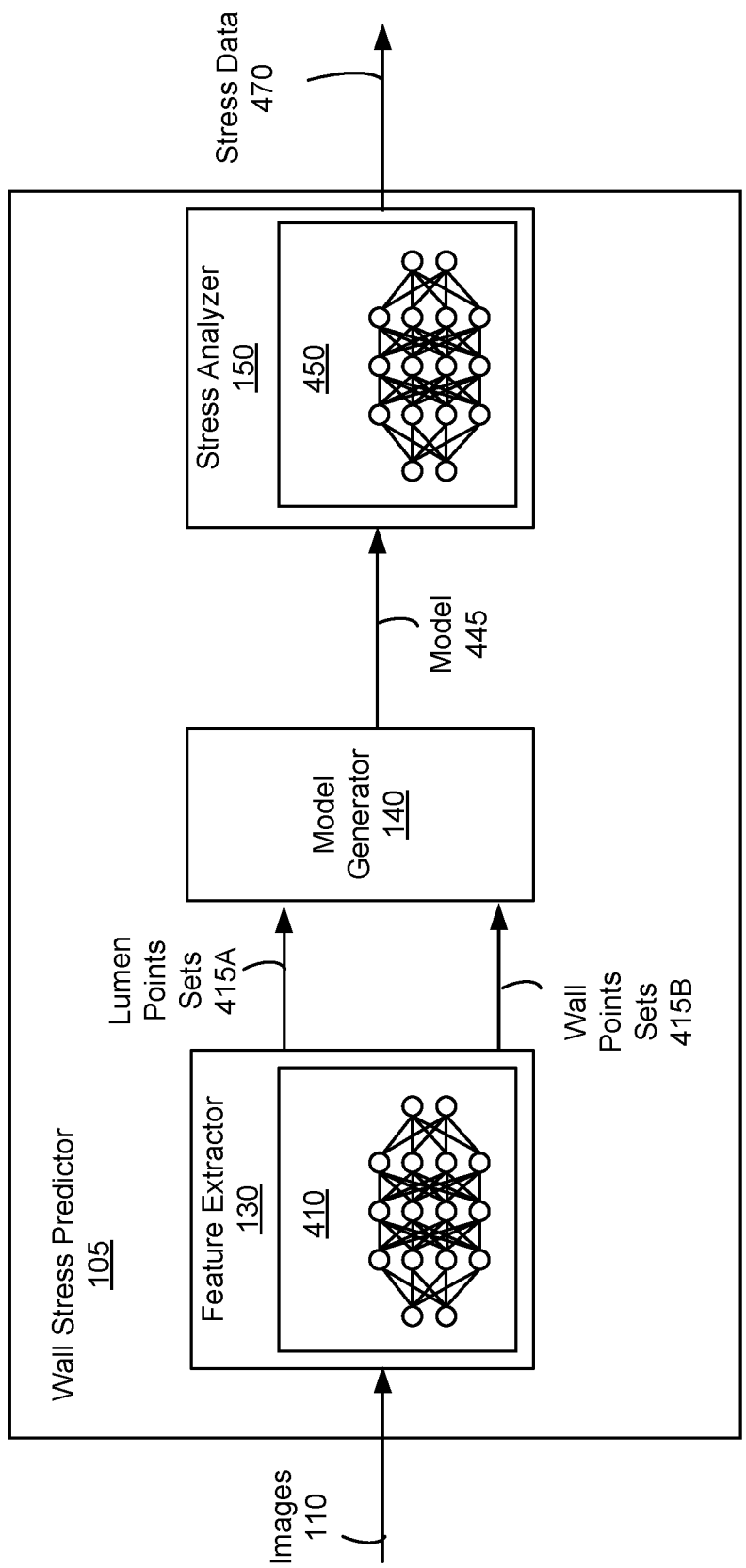
FIG. 4 is a block diagram of a wall stress predictor based on neural networks, according to an example implementation of the present disclosure.

FIG. 4 is a block diagram of a wall stress predictor 105 based on neural networks, according to an example implementation of the present disclosure. In some embodiments, the wall stress predictor 105 includes the feature extractor 130, the model generator 140, and the stress analyzer 150 as described above with respect to FIG. 1. In some embodiments, the wall stress predictor 105 includes more, fewer, or different components than shown in FIG. 1.

In one configuration, the feature extractor 130 is coupled to the model generator 140, and the model generator 140 is coupled to the stress analyzer 150. In this configuration, the feature extractor 130 may detect lumen points sets 415A and wall points sets 415B in the images 110, and provide the lumen points sets 415A and the wall points sets 415B to the model generator 140. The lumen points sets 415A and the wall points sets 415B may be equivalent to or correspond to the lumen points sets 315A and wall points sets 315B of FIG. 3. In some embodiments, the feature extractor 130 includes a machine learning neural network 410 that automatically extracts or detects the lumen points sets 415A and the wall points sets 415B in the images 110. The model generator 140 may receive the lumen points sets 415A and the wall points sets 415B, and can provide a model 445 to the stress analyzer 150. For example, the model generator 140 performs similar processes performed by the mesh generator 320, the ILT model generator 330, the polysurface model generator 334, and the model combiner 340 of FIG. 3. The model 445 may be equivalent to or correspond to the combined model 345 described above with respect to FIG. 3. The stress analyzer 150 may receive the model 445, and generate stress data 470 indicating wall stress of the body part according to the model 445. In some embodiments, the stress analyzer 150 includes a (trained) machine learning neural network 450 that automatically generates stress data 470 based on morphological aspects of the model 445.

In one configuration, the model generator 140 may be omitted or bypassed, and the feature extractor 130 may directly provide the lumen points sets 415A and the wall points sets 415B to the stress analyzer 150. In this configuration, the stress analyzer 150 may simulate, predict, or estimate stress data according to coordinates or locations of the lumen points sets 415A and the wall points sets 415B corresponding to (e.g., inferred) morphological aspects of the model 445 to generate the stress data 470. Hence, computational resources (e.g., processing resources and storage amount) can be reduced, simplified or conserved by bypassing the model generator 140.

Figure 5A:
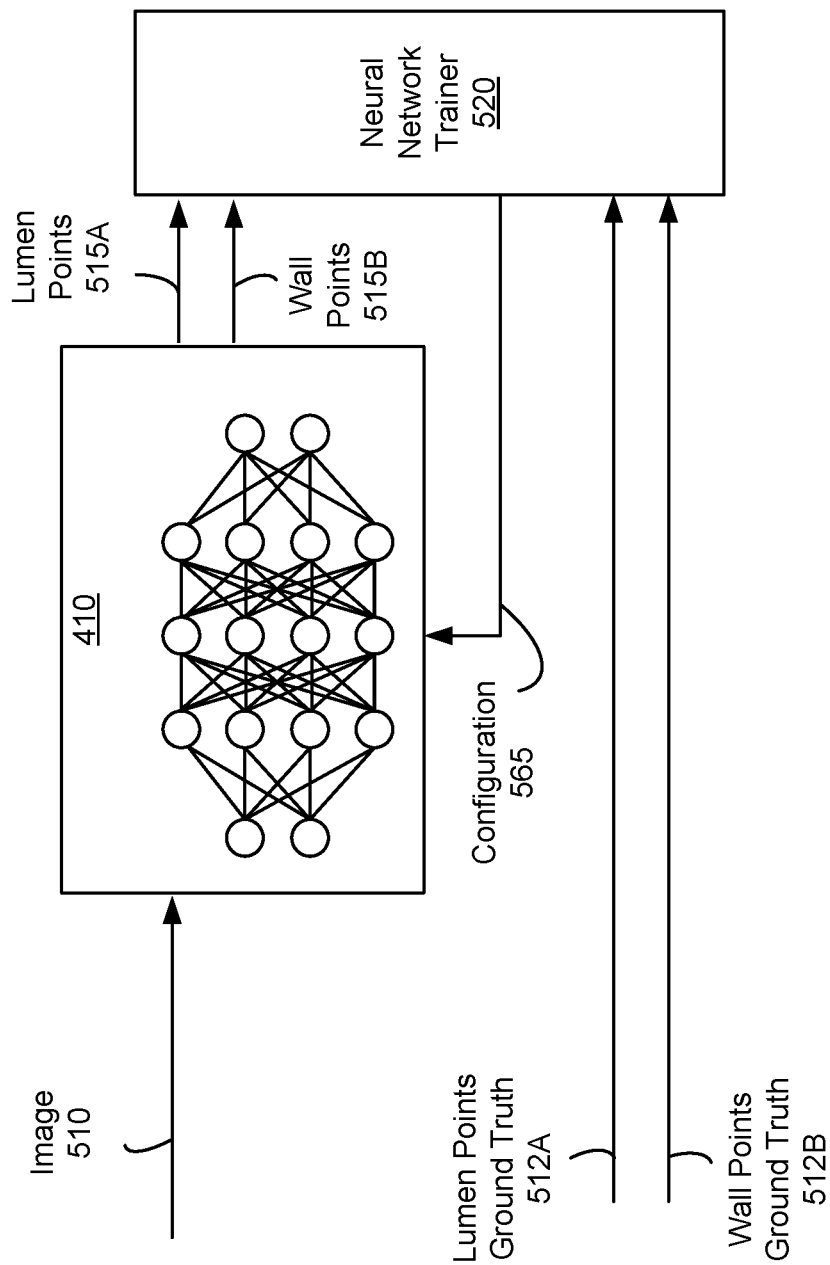
FIG. 5A is a block diagram of a neural network trainer training a neural network of a feature extractor in a training phase, according to an example implementation of the present disclosure.

FIG. 5A is a block diagram of a neural network trainer 520 training the neural network 410 of the feature extractor 130 in a training phase, according to an example implementation of the present disclosure. In some embodiments, the neural network trainer 520 is implemented as part of the system 100, the system 300, or a system implementing both the systems 100, 300. The neural network trainer 520 may be implemented using, for example, Auto Machine Learning (AutoML) including Tree-based Pipeline Optimization Tool (TPOT). In one aspect, the neural network 410 receives an image 510. The image 510 may be a cross sectional image capturing a body part and its surrounding organs or anatomy (or other body parts). For example the image 510 may be one of the images 305. The neural network 410 may automatically detect a set of lumen points 515A and a set of wall points 515B in the image 510 according to a configuration 565 of the neural network 410. Examples of the configuration 565 or parameters include weights and/or bias of nodes of the neural network 410. The neural network trainer 520 may receive the set of lumen points 515A and the set of wall points 515B from the neural network 410. Moreover, the neural network trainer 520 may receive lumen points ground truth 512A and wall points ground truth 512B. The lumen points ground truth 512A and the wall points ground truth 512B may be the set of lumen points 315A and the set of wall points 315B for the image 305 obtained (e.g., from an image recognition/segmentation program, cloud service or platform such as Keras/Tensorflow) through the feature identification interface 310 of FIG. 3.

In some embodiments, the neural network 410 includes a single neural network for the combined ILT geometry for extracting the set of lumen points 515A and for extracting the set of wall points 515B. The neural network trainer 520 may compare the set of lumen points 515A with the lumen points ground truth 512A, and adjust configuration 565 of the first neural network according to the comparison, to reduce errors or differences between the set of lumen points 515A and the lumen points ground truth 512A. Similarly, the neural network trainer 520 may compare the set of wall points 515B with the wall points ground truth 512B, and adjust configuration 565 of the second neural network according to the comparison to reduce errors or differences between the set of wall points 515B and the wall points ground truth 512B. Accordingly, an additional set of lumen points 515A and an additional set of wall points 515B detected for the image 510 by the neural network 410 according to the adjusted configuration 565 can become closer to the lumen points ground truth 512A and the wall points ground truth 512B. The neural network trainer 520 may repeat the process with the same image or with different images with corresponding ground truth to adjust the configuration 565, until the errors of the set of lumen points 515A and the set of wall points 515B output by the neural network 410 with respect to corresponding ground truth become less than a predetermined threshold (e.g., less than 2%). If the errors become less than the predetermined threshold, the neural network trainer 520 may store the adjusted configuration 565 for use during a run time phase.

FIG. 5B is a block diagram of the neural network 410 of the feature extractor 130 in a run time phase, according to an example implementation of the present disclosure. In the run time phase, a cross sectional image 580 may be provided to the neural network 410. The image 580 may be one of the images 110 in FIG. 1. The neural network 410 may automatically detect a set of lumen points 595A and a set of wall points 595B in the image 580, according to weights and/or biases of nodes indicated by the configuration 565. According to the configuration 565 adjusted or determined in the training phase, the neural network 410 can accurately detect a set of lumen points 595A and a set of wall points 595B in the image 580 within a short time period (e.g., less than 5 minutes).

Figure 6:
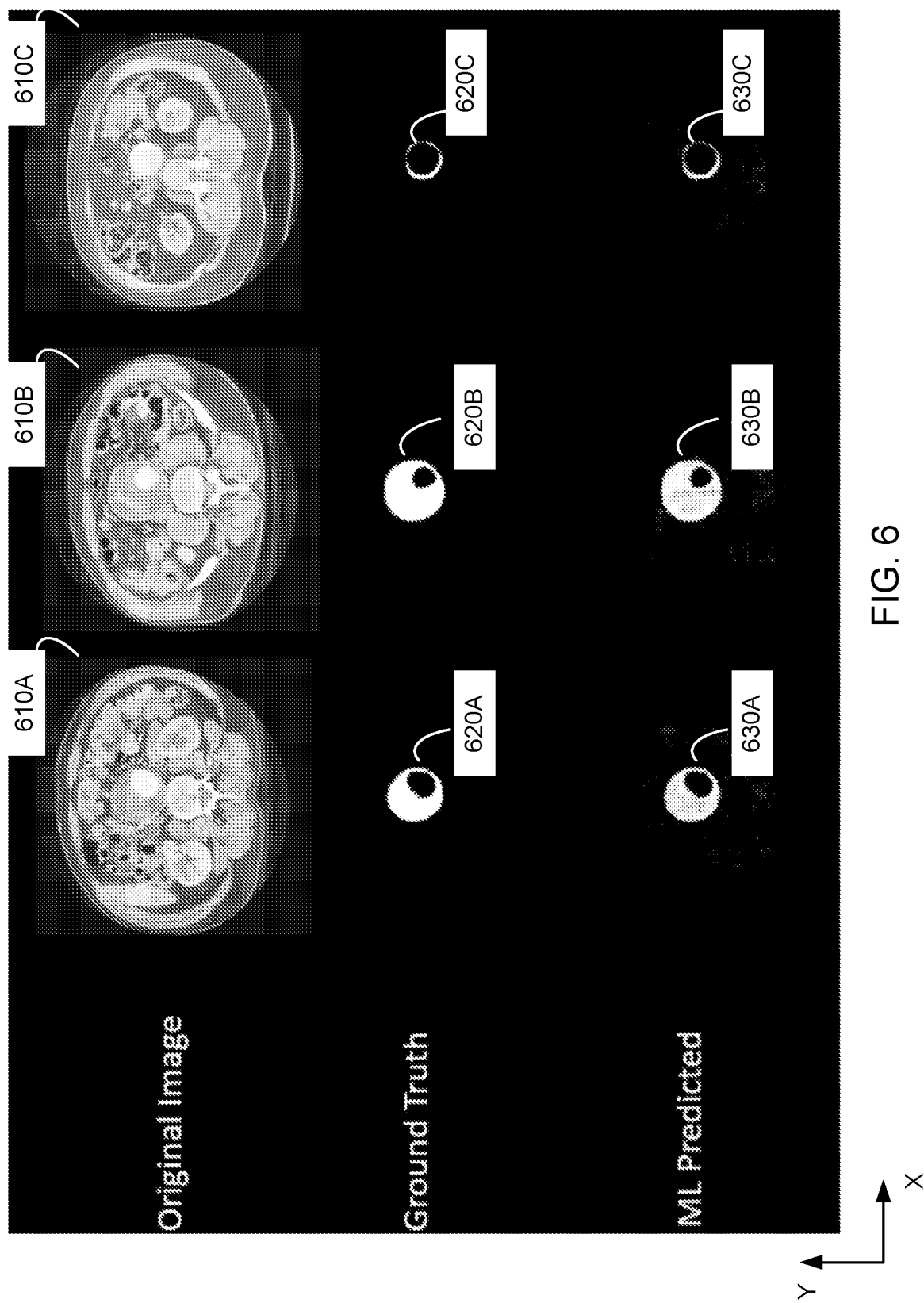
FIG. 6 shows example features extracted from images, according to an example implementation of the present disclosure.

FIG. 6 shows example features 630A-630C extracted from images 610A-610C, according to an example implementation of the present disclosure. In some embodiments, the neural network 410 receives the cross sectional images 610A-610C of a body along a z direction, and automatically detects body parts 630A, 630B, 630C. For example, the neural network 410 detects boundaries of a lumen and a wall of an aorta in the images 610A-610C. The neural network 410 may detect points on the boundaries of the lumen and the wall on the images 610A-610C. Compared to the ground truth 620A-620C, the features detected by the neural network 410 are substantially close to the ground truth 620A-620C.

Figure 7A:
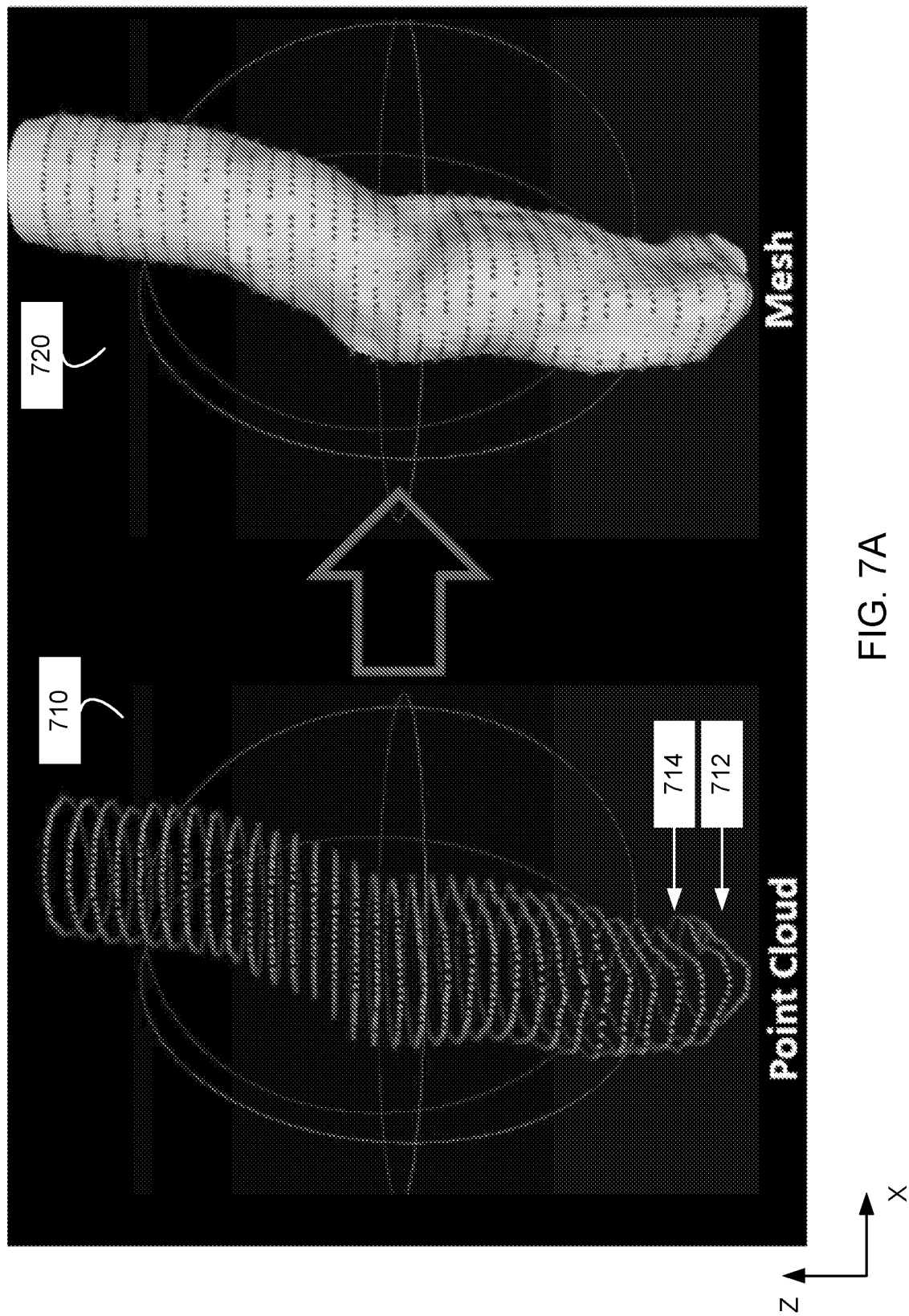
FIGS. 7A-7C show example three dimensional models generated based on features extracted from multiple images, according to an example implementation of the present disclosure.
Figure 7B:
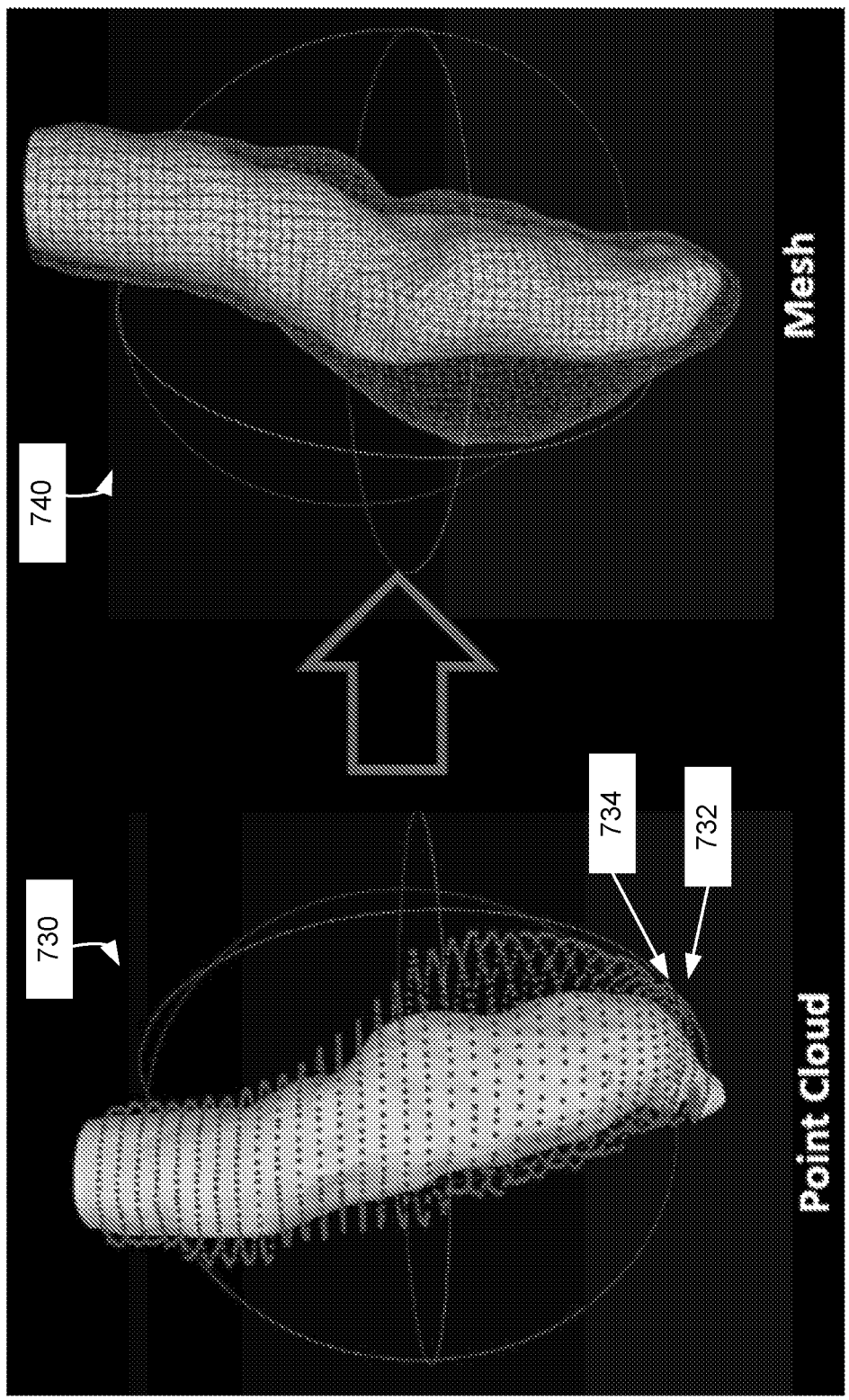

FIGS. 7A-7B show example three dimensional models 720, 740 generated based on features 710, 730 extracted from multiple images (e.g. multiple cross sectional images), according to an example implementation of the present disclosure. In some embodiments, the features 710, 730 include, or are represented by a point cloud. The point cloud may include multiple sets of points, where each set of points is from a corresponding image. For example, referring to FIG. 7A, a set of points 712 corresponds to a boundary of a lumen detected in a first image, and a set of points 714 corresponds to a boundary of the lumen detected in a second image. In one approach, the model generator 140 may connect the sets of points for the lumen to generate the three dimensional mesh model 720 of the lumen. Similarly, referring to FIG. 7B, a set of points 732 corresponds to a boundary of a wall detected in the first image, and a set of points 734 corresponds to a boundary of the wall detected in the second image. In one approach, the model generator 140 may connect the sets of points for the wall to generate the three dimensional mesh model 740 of the wall. The mesh model 740 of the wall and the mesh model 720 of the lumen may be combined into a single mesh model. The model generator 140 may also generate an enhanced three dimensional model having polysurfaces based on the mesh model.

Figure 7C:
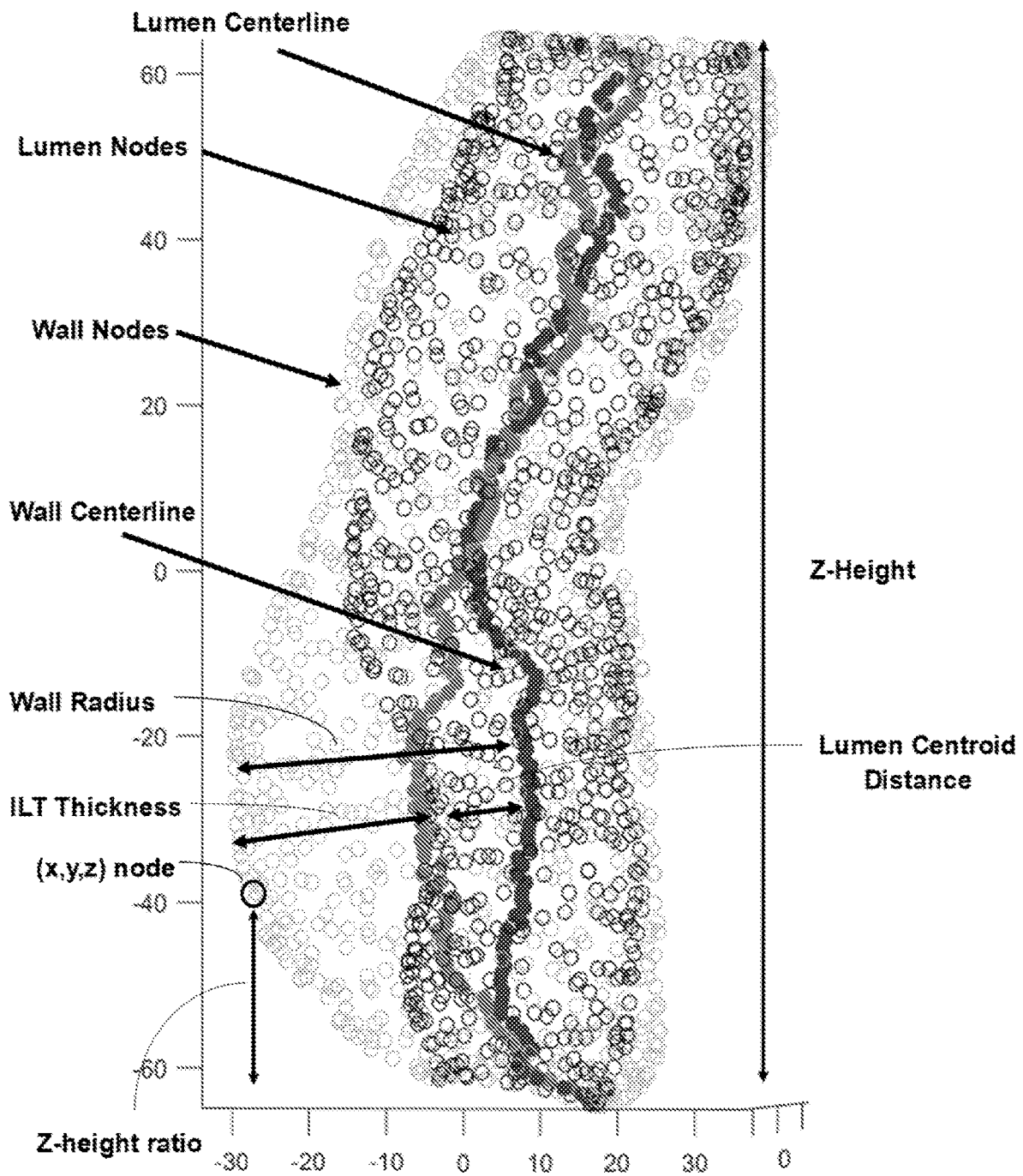

Referring to FIG. 7C, illustrated is a three dimensional model 780 generated based on features extracted from multiple images, according to an example implementation of the present disclosure. In one aspect, FIG. 7C illustrates a shape index for a point in a three dimensional model indicating a x, y, z coordinate, a z-height ratio, a distance to a centroid (or a center line), an intraluminal thrombus thickness, a wall radius, a principal curvature of a neighboring node, tortuosity, and/or a wall to lumen vector, etc., at the point in the three dimensional model 780. These morphological indices can also be normalized to globalize each variable to a population. Shape indices of multiple points of the three dimensional model may be provided to the neural network 450 for predicting wall stress in response to pressure applied.

Figure 8A:
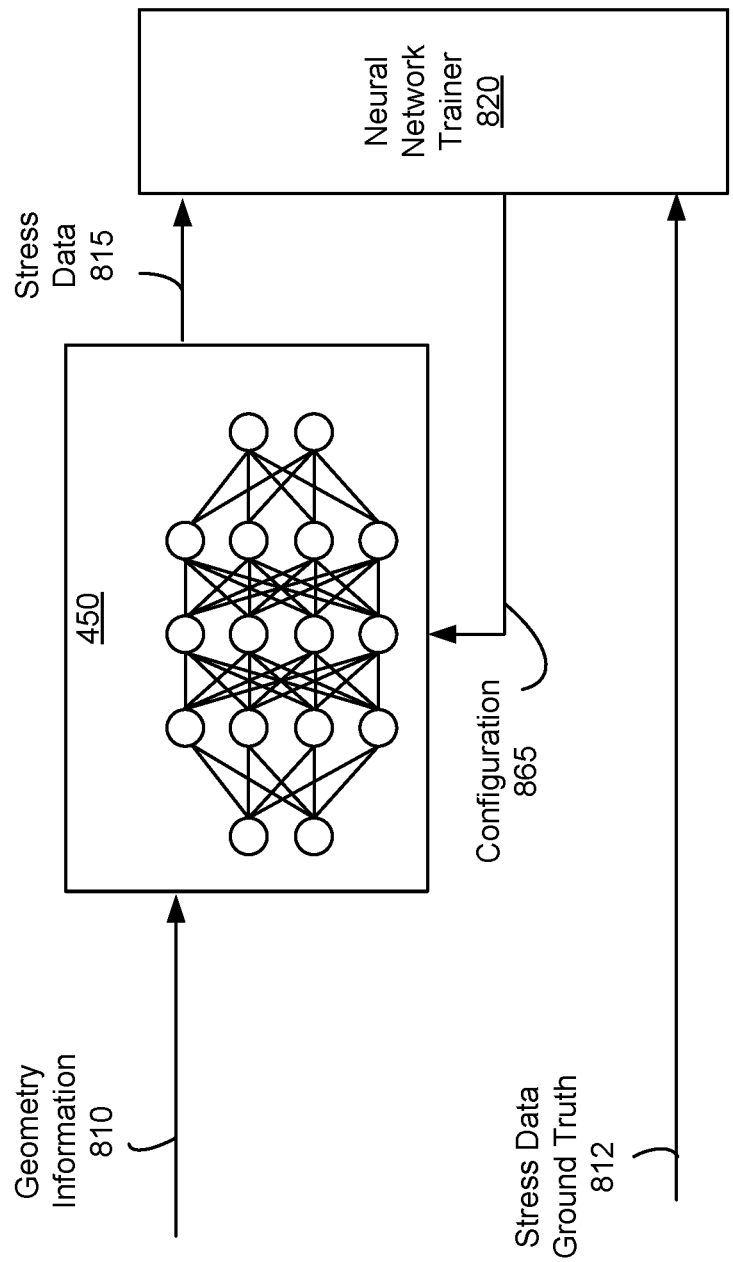
FIG. 8A is a block diagram of a neural network trainer training a neural network of a stress analyzer in a training phase, according to an example implementation of the present disclosure.

FIG. 8A is a block diagram of a neural network trainer 820 training the neural network 450 of the stress analyzer 150 in a training phase, according to an example implementation of the present disclosure. In some embodiments, the neural network trainer 820 is implemented as part of the system 100, the system 300, or a system implementing both the systems 100, 300. The neural network trainer 820 may be implemented using AutoML that may include Tree-based Pipeline Optimization Tool (TPOT). In one aspect, the neural network 450 receives geometry information 810 of a body part (e.g., aorta) indicating morphological aspects of the body part. The geometry information 810 may be the model 445 from the model generator 140, shape indices with associated coordinates, and/or the lumen points set 415A and the wall points sets 415B from the feature extractor 130. The neural network 450 may automatically simulate, estimate, or predict wall stress of the body part to generate stress data 815 according to configuration 865 of the neural network 450. Examples of the configuration 865 or parameters include weights and/or bias of nodes of the neural network 450. The neural network trainer 820 may also receive stress data ground truth 812. The stress data ground truth 812 may be the stress data 355 for the body part from the stress solver 350 of FIG. 3.

The neural network trainer 820 may compare the stress data 815 with the stress data ground truth 812, and adjust configuration 865 of the neural network 450 according to the comparison to reduce errors or differences between the stress data 815 and the stress data ground truth 812. Stress data ground truth 812 can include known or predetermined stress information for (various points on) the body part, for example, von Mises simulation results (from a program such as Abaqus), which can include maximum principal stress, minimum principal stress, etc., at various points on the body part. Accordingly, additional stress data 815 generated for the geometry information 810 by the neural network 450 according to the adjusted configuration 865 can become closer to the stress data ground truth 812. The neural network trainer 820 may repeat the process with the same geometry information 810 or with different geometry information 810 with corresponding ground truth to adjust the configuration 865, until the errors of the stress data 815 with respect to the stress data ground truth 812 become less than a predetermined threshold (e.g., less than 2%). If the errors become less than the predetermined threshold, the neural network trainer 820 may store the adjusted configuration 865 for use during a run time phase.

Figure 8B:
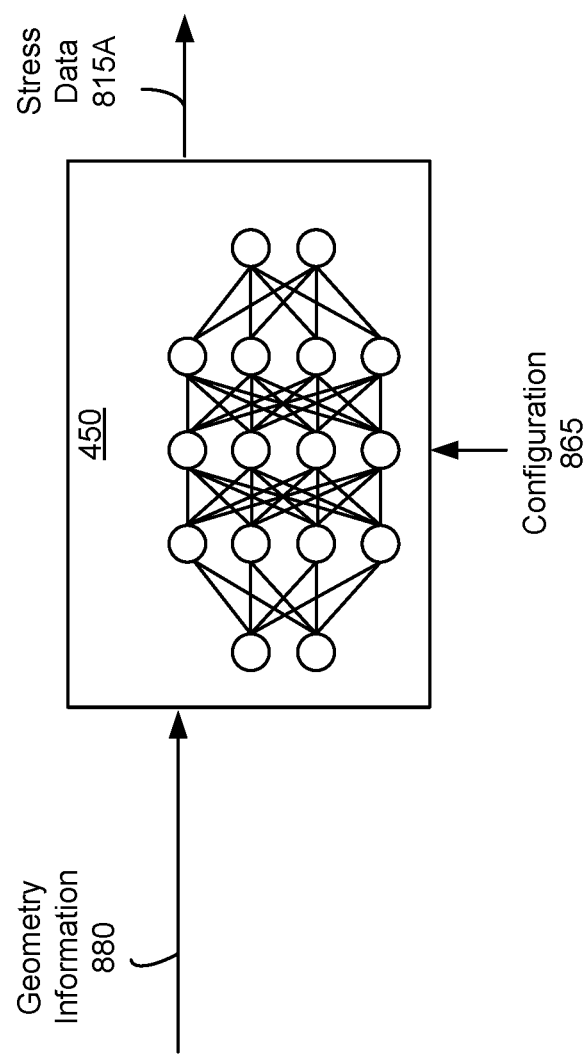
FIG. 8B is a block diagram of a neural network of a stress analyzer in a run time phase, according to an example implementation of the present disclosure.

FIG. 8B is a block diagram of the neural network 450 of the stress analyzer 150 in a run time phase, according to an example implementation of the present disclosure. In the run time phase, geometry information 880 may be provided to the neural network 450. The geometry information 880 may be the model 445 or the lumen point sets 415A and the wall point sets 415B of FIG. 4. The geometry information may include shape indices and location information (e.g., Cartesian coordinates) of the shape indices. For example, the shape indices include at least one of: a z-height ratio, a distance to a centroid, an ILT thickness, a principal curvature of a neighboring node, tortuosity, or a wall to lumen vector, etc. Without performing convoluted computation for wall stress for each point according to the stress solver 350, the neural network 450 can mimic the performance of the stress solver 350 by automatically simulating, estimating, or predicting, wall stress of a body part according to morphological aspects of the body part as indicated by the geometry information 880 and weights and/or biases of nodes of the neural network 450 indicated by the configuration 865. Hence, according to the configuration 865 adjusted or determined in the training phase, the neural network 450 can accurately predict wall stress within a short time period (e.g., less than 10 seconds).

Figure 9:
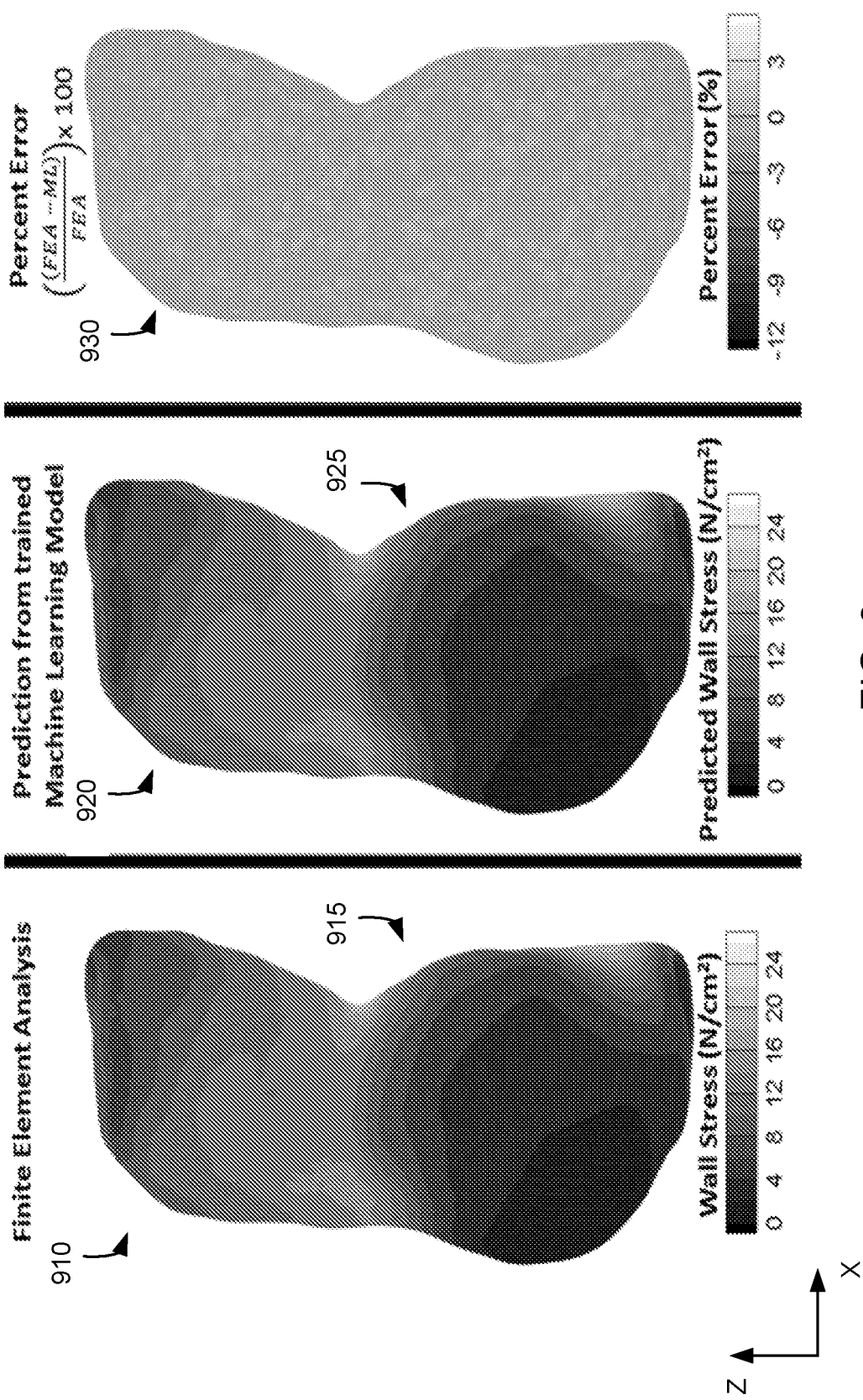
FIG. 9 shows a comparison of output of a wall stress predictor against ground truth, according to an example implementation of the present disclosure.

FIG. 9 shows a comparison of an output 920 of the wall stress predictor 105 against the ground truth 910, according to an example implementation of the present disclosure. The ground truth 910 may be the stress data 355 rendered in a three dimensional model, and the output 920 may be the stress data 470 rendered in a three dimensional model. As shown in FIG. 9, the ground truth 910 has a portion 915 that is subject to a high risk of rupture, and the output 920 of the wall stress predictor 105 also has a portion 925 that is subject to a high risk of rupture, where the portion 915 of the ground truth 910 is substantially close to the portion 925 of the output 920 of the wall stress predictor 105. Moreover, as shown by a difference model 930, differences between the ground truth 910 and the output 920 of the wall stress predictor 105 are generally negligible (e.g., less than 1%). Hence, the wall stress predictor 105 can predict wall stress in a short time period (e.g., less than 10 minutes) without high accuracy.

Figure 10:
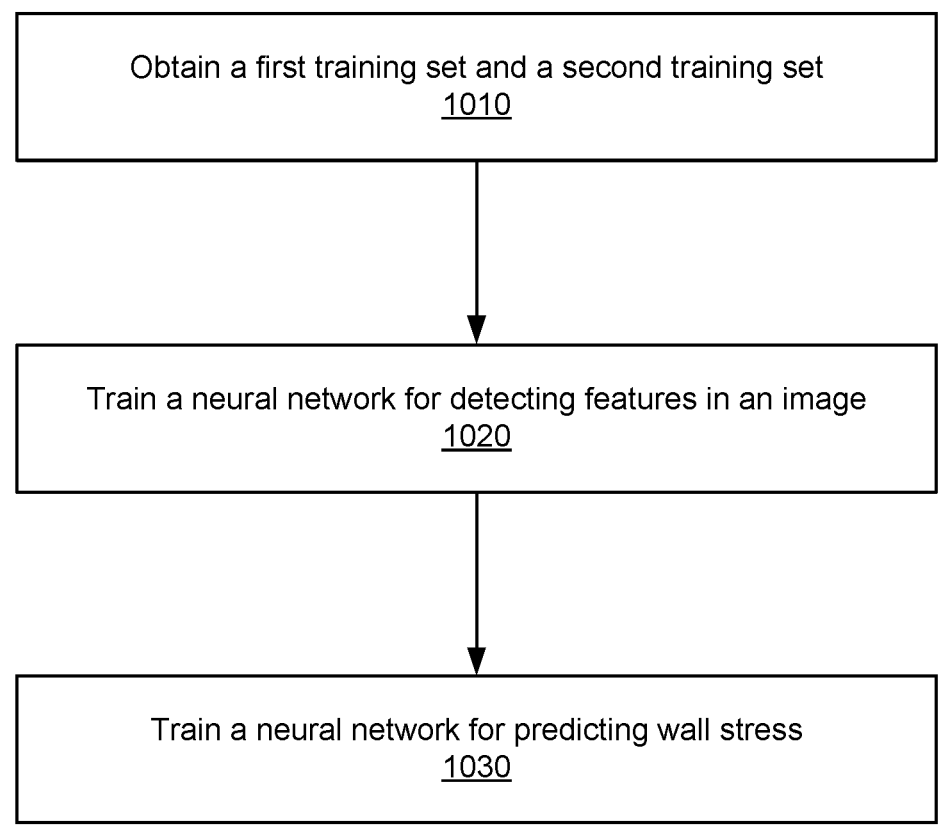
FIG. 10 is a flow chart illustrating a process of training neural networks for predicting wall stress of a body part, according to an example implementation of the present disclosure.

FIG. 10 is a flow chart illustrating a process 1000 of training neural networks for predicting wall stress of a body part in a training phase, according to an example implementation of the present disclosure. In some embodiments, the process 1000 is performed by the system 300, the neural network trainer 520 and the neural network trainer 820. In some embodiments, the system 300, the neural network trainer 520, and the neural network trainer 820 are implemented by a single system or implemented by separate systems. In some embodiments, the process 1000 is performed by other entities. In some embodiments, the process 1000 includes more, fewer, or different steps than shown in FIG. 10.

In one approach, the system 300 obtains 1010 a first training set and a second training set. The first training set may include images capturing cross sections of a body part (e.g., aorta) and its surrounding body parts, and features of body part in the images. Examples of the features include points on boundaries (e.g., lumen, wall, etc.) of the body part. The second training set may include geometry information indicating morphological aspects of a body part (or a three dimensional model of the body part) and associated wall stress of the body part. For example, the geometry information may include shape indices and location information (e.g., Cartesian coordinates) of the shape indices. For example, the shape indices include at least one of: a z-height ratio, a distance to a centroid, an ILT thickness, a principal curvature of a neighboring node, tortuosity, or a wall to lumen vector, etc.

In some embodiments, the first training set and the second training set are generated by or in conjunction with the system 300. For example, the system 300 presents a user interface allowing a user operating the system 300 to manually select boundaries (e.g., wall, lumen, etc.) or points on the boundaries of a body part (e.g., aorta) in images. The system 300 may generate the model 345 including geometry information of the body part according to points on the boundaries of the body part in the images, and compute, for each point or for each surface formed by various points, wall stress of the body part.

In one approach, the neural network trainer 520 trains 1020 a neural network for detecting features in an image. The neural network may be the neural network 410 of the feature extractor 130 in FIG. 4. The neural network 410 for detecting features in the image may include separate neural networks: a first neural network for detecting a set of points for inner boundary of a body part and a second neural network for detecting a set of points for outer boundary of the body part. Alternatively, the neural network 410 for detecting features in the image may include a single neural network that can detect points for the inner boundary and the inner boundary of the body part. The neural network trainer 520 may compare the set of points detected by the neural network 410 with corresponding ground truth, and adjust configuration (e.g., weights and/or biases of nodes of the neural network) of the first neural network according to the comparison to reduce errors or differences between the set of points and the corresponding ground truth. Accordingly, an additional set of points detected by the neural network according to the adjusted configuration can become closer to the corresponding ground truth. The neural network trainer 520 may repeat the process with the same image or with different images with corresponding ground truth to adjust the configuration, until the errors of the set of points output by the neural network with respect to corresponding ground truth become acceptable, e.g., less than a predetermined threshold (e.g., less than 2%). If the errors become less than the predetermined threshold, the neural network trainer 520 may store the adjusted configuration for use during a run time phase.

In one approach, the neural network trainer 820 trains 1030 a neural network for predicting wall stress of a body part according to localized or global geometry information. The neural network trainer 820 may compare stress data output by the neural network with the ground truth and adjust configuration of the neural network according to the comparison to reduce errors or differences between the stress data and the ground truth. Accordingly, additional stress data output by the neural network for the geometry information according to the adjusted configuration can become closer to the ground truth. The neural network trainer 820 may repeat the process with the same geometry information or with different geometry information with corresponding ground truth to adjust the configuration, until the errors of the stress data with respect to the ground truth become less than a predetermined threshold (e.g., less than 2%). If the errors become less than the predetermined threshold, the neural network trainer 820 may store the adjusted configuration 865 for use during a run time phase. Although in FIG. 10, the step 1030 is performed after the step 1020, in some embodiments, the steps 1020, 1030 can be performed in a different order, or simultaneously.

Figure 11:
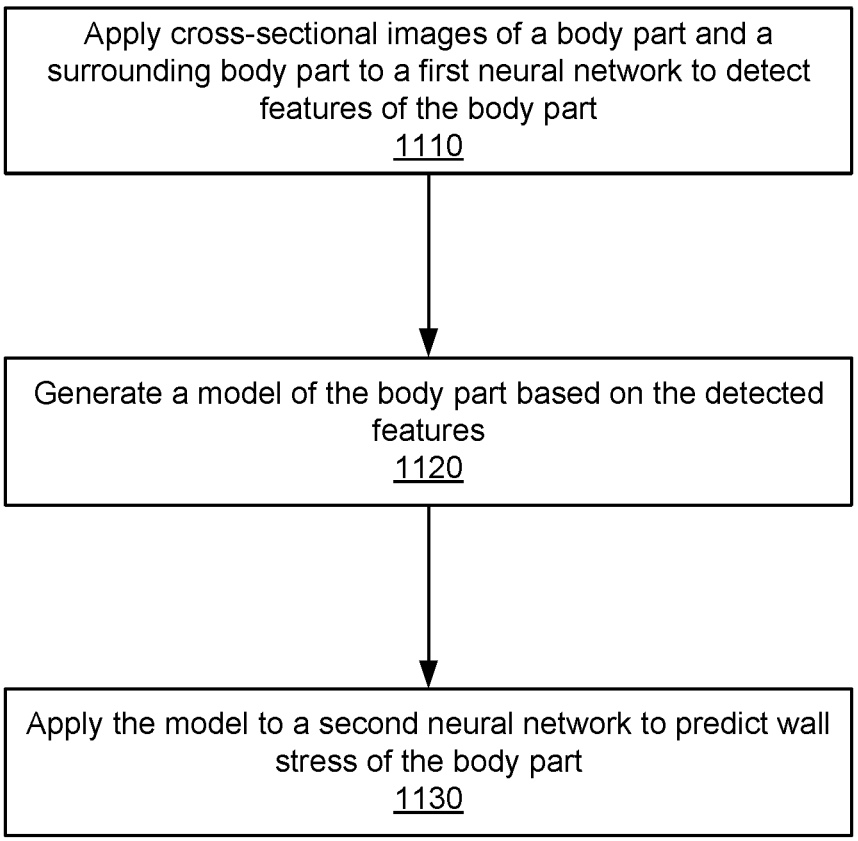
FIG. 11 is a flow chart illustrating a process of predicting wall stress of a body part based on neural networks, according to an example implementation of the present disclosure.

FIG. 11 is a flow chart illustrating a process 1100 of predicting wall stress of a body part based on neural networks in a run time phase, according to an example implementation of the present disclosure. The process 1100 may be performed by the system 100. In some embodiments, the process 1100 is performed by other entities. In some embodiments, the process 1100 includes more, fewer, or different components than shown in FIG. 11.

In one approach, the system 100 applies 1110 cross-sectional images of a body part and a surrounding body part to a first neural network (e.g., neural network 410) to detect features of the body part. The features may be outer boundaries and inner boundaries of the body part. For each image, the system 100 may automatically detect a set of lumen points and a set of wall points in the image via the first neural network trained in the training phase. For example, configuration determined or adjusted in the training phase can be applied to the first neural network for detecting the set of lumen points and the set of wall points. In one aspect, the system 100 can automatically detect features (e.g., sets of lumen points and sets of wall points) in multiples images, via the first neural network, within a short time period (e.g., less than 5 minutes) with high accuracy.

In one approach, the system 100 generates 1120 a model of a body part based on the detected features. For example, the system 100 may receive sets of lumen points of the body part in the images and generate a mesh model of a lumen by connecting the sets of lumen points. Similarly, the system 100 may receive sets of wall points of the body part in the images and generate a mesh model of a wall by connecting the sets of wall points. Based on the mesh models, the system 100 may generate a single model including geometry information of the body part. For example, the geometry information includes shape index for different points of the model, where a shape index for a point in a three dimensional model may indicate a x, y, z coordinate, a z-height ratio, a distance to a centroid (or a center line), an intraluminal thrombus thickness, a wall radius, a principal curvature of a neighboring node, tortuosity, and/or a wall to lumen vector, etc. at the point.

In one approach, the system 100 applies 1130 the model to a second neural network (e.g., neural network 450) to predict wall stress of the body part. Without computing wall stress for each point of the model, the system 100 can automatically simulate, estimate, or predict, wall stress of the body part, via the second neural network, according to morphological aspects of the body part as indicated by the model or the geometry information of the model. For example, configuration determined or adjusted in the training phase can be applied to the second neural network for predicting wall stress of the body part. According to the configuration adjusted or determined in the training phase, the system 100 can accurately predict wall stress within a short time period (e.g., less than 10 seconds) via the second neural network.

In some embodiments, the process 1100 includes detecting, by a first neural network, from a first image of a first cross section of a body part and its surrounding body part, a first outer boundary of the first cross section of the body part and a first inner boundary of the first cross section of the body part. The process 1100 may include detecting, by the first neural network, from a second image of a second cross section of the body part and the surrounding body part, a second outer boundary of the second cross section of the body part and a second inner boundary of the second cross section of the body part. The process 1100 may include predicting, by a second neural network, wall stress of the body part, according to geometry information derived from the first outer boundary, the first inner boundary, the second outer boundary and the second inner boundary.

In certain embodiments, the process 1100 is used to evaluate the risk of an abdominal aortic aneurysm (AAA), a ventricular aneurysm, a brain aneurysm, or any other type or form of aneurysm. The process 1100 is used in connection with any body part that has a tubular structure and/or a wall-like or lining-like structure. The body part can be or include a human body part selected from the group consisting of aorta, artery, ureter, intestine, and heart. In certain embodiments, the process 1100 (or any method, sub process or step described herein) can be completed in a time period of less than about 15 minutes. In certain embodiments, the process 1100 (or any method, sub process or step described herein) can be completed in a time period of less than about 14 minutes, less than about 13 minutes, less than about 12 minutes, less than about 11 minutes, less than about 10 minutes, less than about 9 minutes, less than about 8 minutes, less than about 7 minutes, less than about 6 minutes, or about 5 minutes or less. In some embodiments, the process 1100 (or any method, sub process or step described herein) can be completed in a time period of less than about 4 minutes, less than about 3 minutes, less than about 2 minutes, less than about 1 minute, less than about 45 sec, less than about 30 sec, less than about 20 sec, less than about 15 sec, or about 10 sec or less.

Figure 12:
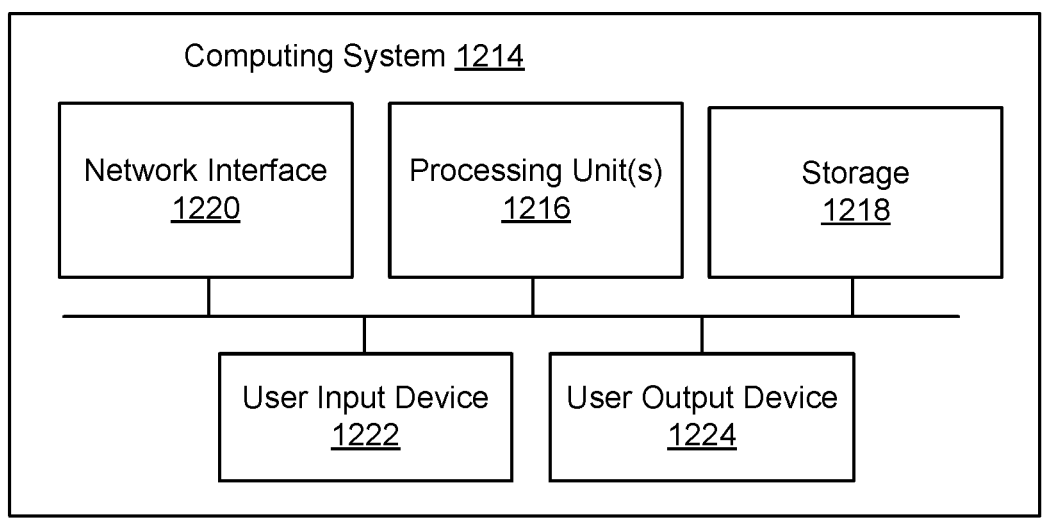
FIG. 12 is a block diagram of a computing environment according to an example implementation of the present disclosure.

Various operations described herein can be implemented on computer systems. FIG. 12 shows a block diagram of a representative computing system 1214 usable to implement the present disclosure. In some embodiments, the system 100, the system 300, a combination of the systems 100, 300 is implemented by the computing system 1214. Computing system 1214 can be implemented, for example, as a consumer device such as a smartphone, other mobile phone, tablet computer, wearable computing device (e.g., smart watch, eyeglasses, head mounted display), desktop computer, laptop computer, cloud computing service or implemented with distributed computing devices. In some embodiments, the computing system 1214 can include computer components such as processors 1216, storage device 1218, network interface 1220, user input device 1222, and user output device 1224.

Network interface 1220 can provide a connection to a wide area network (e.g., the Internet) to which WAN interface of a remote server system is also connected. Network interface 1220 can include a wired interface (e.g., Ethernet) and/or a wireless interface implementing various RF data communication standards such as Wi-Fi, Bluetooth, or cellular data network standards (e.g., 3G, 4G, 5G, 60 GHz, LTE, etc.).

User input device 1222 can include any device (or devices) via which a user can provide signals to computing system 1214; computing system 1214 can interpret the signals as indicative of particular user requests or information. User input device 1222 can include any or all of a keyboard, touch pad, touch screen, mouse or other pointing device, scroll wheel, click wheel, dial, button, switch, keypad, microphone, sensors (e.g., a motion sensor, an eye tracking sensor, etc.), and so on.

User output device 1224 can include any device via which computing system 1214 can provide information to a user. For example, user output device 1224 can include a display to display images generated by or delivered to computing system 1214. The display can incorporate various image generation technologies, e.g., a liquid crystal display (LCD), light-emitting diode (LED) including organic light-emitting diodes (OLED), projection system, cathode ray tube (CRT), or the like, together with supporting electronics (e.g., digital-to-analog or analog-to-digital converters, signal processors, or the like). A device such as a touchscreen that function as both input and output device can be used. Output devices 1224 can be provided in addition to or instead of a display. Examples include indicator lights, speakers, tactile "display" devices, printers, and so on.

Some implementations include electronic components, such as microprocessors, storage and memory that store computer program instructions in a non-transitory computer readable storage medium. Many of the features described in this specification can be implemented as processes that are specified as a set of program instructions encoded on a computer readable storage medium. When these program instructions are executed by one or more processors, they cause the processors to perform various operation indicated in the program instructions. Examples of program instructions or computer code include machine code, such as is produced by a compiler, and files including higher-level code that are executed by a computer, an electronic component, or a microprocessor using an interpreter. Through suitable programming, processor 1216 can provide various functionality for computing system 1214, including any of the functionality described herein as being performed by a server or client, or other functionality associated with message management services.

It will be appreciated that computing system 1214 is illustrative and that variations and modifications are possible. Computer systems used in connection with the present disclosure can have other capabilities not specifically described here. Further, while computing system 1214 is described with reference to particular blocks, it is to be understood that these blocks are defined for convenience of description and are not intended to imply a particular physical arrangement of component parts. For instance, different blocks can be located in the same facility, in the same server rack, or on the same motherboard. Further, the blocks need not correspond to physically distinct components. Blocks can be configured to perform various operations, e.g., by programming a processor or providing appropriate control circuitry, and various blocks might or might not be reconfigurable depending on how the initial configuration is obtained. Implementations of the present disclosure can be realized in a variety of apparatus including electronic devices implemented using any combination of circuitry and software.

Having now described some illustrative implementations, it is apparent that the foregoing is illustrative and not limiting, having been presented by way of example. In particular, although many of the examples presented herein involve specific combinations of method acts or system elements, those acts and those elements can be combined in other ways to accomplish the same objectives. Acts, elements and features discussed in connection with one implementation are not intended to be excluded from a similar role in other implementations or implementations.

The hardware and data processing components used to implement the various processes, operations, illustrative logics, logical blocks, modules and circuits described in connection with the embodiments disclosed herein may be implemented or performed with a general purpose single- or multi-chip processor, a digital signal processor (DSP), an application specific integrated circuit (ASIC), a field programmable gate array (FPGA), or other programmable logic device, discrete gate or transistor logic, discrete hardware components, or any combination thereof designed to perform the functions described herein. A general purpose processor may be a microprocessor, or, any conventional processor, controller, microcontroller, or state machine. A processor also may be implemented as a combination of computing devices, such as a combination of a DSP and a microprocessor, a plurality of microprocessors, one or more microprocessors in conjunction with a DSP core, or any other such configuration. In some embodiments, particular processes and methods may be performed by circuitry that is specific to a given function. The memory (e.g., memory, memory unit, storage device, etc.) may include one or more devices (e.g., RAM, ROM, Flash memory, hard disk storage, etc.) for storing data and/or computer code for completing or facilitating the various processes, layers and modules described in the present disclosure. The memory may be or include volatile memory or non-volatile memory, and may include database components, object code components, script components, or any other type of information structure for supporting the various activities and information structures described in the present disclosure. According to an exemplary embodiment, the memory is communicably connected to the processor via a processing circuit and includes computer code for executing (e.g., by the processing circuit and/or the processor) the one or more processes described herein.

Methods: In one aspect of the disclosure, encompassed is a method of evaluating a subject who is a member of a patient population at risk for an aneurysm. Aneurysms are classified by their location in the body. The arteries of the brain and heart are the two most common sites of a serious aneurysm. Examples of aneurysms include but are not limited to brain or cerebral aneurysms, aortic or heart aneurysms, ventricular aneurysms, arterial aneurysms, peripheral aneurysms, and aneurysms of the ureter and intestine. A cerebral aneurysm (also known as a brain aneurysm) is a weak or thin spot on an artery in the brain that balloons or bulges out and fills with blood. The bulging aneurysm can put pressure on the nerves or brain tissue. It may also burst or rupture, spilling blood into the surrounding tissue (called a hemorrhage). A ruptured aneurysm can cause serious health problems such as hemorrhagic stroke, brain damage, coma, and even death. A larger brain aneurysm that is steadily growing may press on tissues and nerves causing: pain above and behind the eye, numbness, weakness, paralysis on one side of the face, a dilated pupil in the eye, and/or vision changes or double vision.

Risk factors for developing a cerebral aneurysm include, for example, (1) inherited risk factors, including genetic connective tissue disorders that weaken artery walls, polycystic kidney disease (in which numerous cysts form in the kidneys), arteriovenous malformations (snarled tangles of arteries and veins in the brain that disrupt blood flow, and/or history of aneurysm in a first-degree family member (child, sibling, or parent); (2) other risk factors develop over time and include: untreated high blood pressure, cigarette smoking, drug abuse (especially cocaine or amphetamines, which raise blood pressure to dangerous levels), and age over 40; and (3) less common risk factors include: head trauma, brain tumor, infection in the arterial wall (mycotic aneurysm). Additionally, high blood pressure, cigarette smoking, diabetes, and high cholesterol puts one at risk of atherosclerosis (a blood vessel disease in which fats build up on the inside of artery walls), which can increase the risk of developing a fusiform aneurysm.

Aortic aneurysms are aneurysms that occur in the aorta, the main artery carrying oxygen-rich blood to your body. There are two types of aneurysms that affect the aorta: abdominal and thoracic aortic aneurysms. Risk factors include (1) age, as the risk for aortic aneurysms goes up with age; abdominal aortic aneurysms are most common in adults after age 65. (2) Family history and genetics: several familial or genetic conditions increase the risk for a thoracic aortic aneurysm. These include Ehlers-Danlos syndrome, Loeys-Dietz syndrome, Marfan syndrome, Turner syndrome, Familial thoracic aortic aneurysms, and Bicuspid aortic valve (BAV), which is an abnormal aortic valve. Abdominal aortic aneurysms also run in families. One in 10 people with abdominal aortic aneurysms have a family history of abdominal aortic aneurysms. The chance of developing an abdominal aortic aneurysm is 1 in 5 for people who have a first degree relative with the condition, which means a parent, brother, sister, or child was affected. (3) Lifestyle habits: some lifestyle habits increase the risk of having an aortic aneurysm. These include (i) cigarette smoking, which increases the risk for an aortic aneurysm, especially an abdominal aortic aneurysm; (ii) using stimulants such as cocaine; and (iii) weight lifting. (4) Medical conditions: Medical conditions that are risk factors for aortic aneurysms include: aneurysms of blood vessels in other parts of your body; chronic obstructive pulmonary disease (COPD); cardiovascular conditions, such as atherosclerosis, ischemic heart disease, and peripheral artery disease; high blood cholesterol; high blood pressure, the leading risk factor for thoracic aortic aneurysms but also a risk factor for abdominal aortic aneurysm; infection, a risk factor for thoracic aortic aneurysms. Such a case is known as an infective thoracic aortic aneurysm and is usually caused by bacteria; kidney conditions, such as chronic renal insufficiency, chronic kidney disease, and polycystic kidney disease; obesity; pheochromocytomaexternal link, a rare tumor of the adrenal gland that can lead to high blood pressure; trauma, such as from car accidents or falls, a risk factor for thoracic aortic aneurysms; and vasculitis. (5) Finally, men are more likely than women to develop aortic aneurysms.

Peripheral aneurysms: An aneurysm can also occur in a peripheral artery. Types of peripheral aneurysm include: (i) Popliteal aneurysm: this happens behind the knee. It is the most common peripheral aneurysm; (ii) splenic artery aneurysm: this type of aneurysm occurs near the spleen; (iii) mesenteric artery aneurysm: this affects the artery that transports blood to the intestines; (iv) femoral artery aneurysm: the femoral artery is in the groin; (v) carotid artery aneurysm: this occurs in the neck; and (vi) visceral aneurysm: this is a bulge of the arteries that supply blood to the bowel or kidneys. Lifestyle risk factors also relate to peripheral aneurysms, including smoking tobacco, hypertension, inactive lifestyle, and obesity.

The present disclosure contemplates methods, systems and program products on any machine-readable media for accomplishing various operations. The embodiments of the present disclosure may be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. Combinations of the above are also included within the scope of machine-readable media. Machine-executable instructions include, for example, instructions and data which cause a general purpose computer, special purpose computer, or special purpose processing machines to perform a certain function or group of functions.

The phraseology and terminology used herein is for the purpose of description and should not be regarded as limiting. The use of "including" "comprising" "having" "containing" "involving" "characterized by" "characterized in that" and variations thereof herein, is meant to encompass the items listed thereafter, equivalents thereof, and additional items, as well as alternate implementations consisting of the items listed thereafter exclusively. In one implementation, the systems and methods described herein consist of one, each combination of more than one, or all of the described elements, acts, or components.

Any references to implementations or elements or acts of the systems and methods herein referred to in the singular can also embrace implementations including a plurality of these elements, and any references in plural to any implementation or element or act herein can also embrace implementations including only a single element. References in the singular or plural form are not intended to limit the presently disclosed systems or methods, their components, acts, or elements to single or plural configurations. References to any act or element being based on any information, act or element can include implementations where the act or element is based at least in part on any information, act, or element.

Any implementation disclosed herein can be combined with any other implementation or embodiment, and references to "an implementation," "some implementations," "one implementation" or the like are not necessarily mutually exclusive and are intended to indicate that a particular feature, structure, or characteristic described in connection with the implementation can be included in at least one implementation or embodiment. Such terms as used herein are not necessarily all referring to the same implementation. Any implementation can be combined with any other implementation, inclusively or exclusively, in any manner consistent with the aspects and implementations disclosed herein.

Where technical features in the drawings, detailed description or any claim are followed by reference signs, the reference signs have been included to increase the intelligibility of the drawings, detailed description, and claims. Accordingly, neither the reference signs nor their absence have any limiting effect on the scope of any claim elements. Technical and scientific terms used herein have the meanings commonly understood by one of ordinary skill in the art, unless otherwise defined. Any suitable materials and/or methodologies known to those of ordinary skill in the art can be utilized in carrying out the methods described herein.

Systems and methods described herein may be embodied in other specific forms without departing from the characteristics thereof. As used herein, "approximately," "about" "substantially" or other terms of degree will be understood by persons of ordinary skill in the art and will vary to some extent on the context in which it is used. If there are uses of the term which are not clear to persons of ordinary skill in the art given the context in which it is used, references to "approximately," "about" "substantially" or other terms of degree shall include variations of +/−10% from the given measurement, unit, or range unless explicitly indicated otherwise.

Coupled elements can be electrically, mechanically, or physically coupled with one another directly or with intervening elements. Scope of the systems and methods described herein is thus indicated by the appended claims, rather than the foregoing description, and changes that come within the meaning and range of equivalency of the claims are embraced therein.

The term "coupled" and variations thereof includes the joining of two members directly or indirectly to one another. Such joining may be stationary (e.g., permanent or fixed) or moveable (e.g., removable or releasable). Such joining may be achieved with the two members coupled directly with or to each other, with the two members coupled with each other using a separate intervening member and any additional intermediate members coupled with one another, or with the two members coupled with each other using an intervening member that is integrally formed as a single unitary body with one of the two members. If "coupled" or variations thereof are modified by an additional term (e.g., directly coupled), the generic definition of "coupled" provided above is modified by the plain language meaning of the additional term (e.g., "directly coupled" means the joining of two members without any separate intervening member), resulting in a narrower definition than the generic definition of "coupled" provided above. Such coupling may be mechanical, electrical, or fluidic.

References to "or" can be construed as inclusive so that any terms described using "or" can indicate any of a single, more than one, and all of the described terms. A reference to "at least one of 'A' and 'B'" can include only 'A', only 'B', as well as both 'A' and 'B'. Such references used in conjunction with "comprising" or other open terminology can include additional items.

Modifications of described elements and acts such as variations in sizes, dimensions, structures, shapes and proportions of the various elements, values of parameters, mounting arrangements, use of materials, colors, orientations can occur without materially departing from the teachings and advantages of the subject matter disclosed herein. For example, elements shown as integrally formed can be constructed of multiple parts or elements, the position of elements can be reversed or otherwise varied, and the nature or number of discrete elements or positions can be altered or varied. Other substitutions, modifications, changes and omissions can also be made in the design, operating conditions and arrangement of the disclosed elements and operations without departing from the scope of the present disclosure.

References herein to the positions of elements (e.g., "top," "bottom," "above," "below") are merely used to describe the orientation of various elements in the FIGURES. The orientation of various elements may differ according to other exemplary embodiments, and that such variations are intended to be encompassed by the present disclosure.

As used herein "subject," "patient," or "individual" refers to any subject, patient, or individual, and the terms are used interchangeably herein. In this regard, the terms "subject," "patient," and "individual" includes mammals, and, in particular humans. When used in conjunction with "in need thereof," the term "subject," "patient," or "individual" intends any subject, patient, or individual having or at risk for a specified symptom or disorder.

While certain embodiments have been illustrated and described, it should be understood that changes and modifications can be made therein in accordance with ordinary skill in the art without departing from the technology in its broader aspects as defined in the following claims.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, which can of course vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof, inclusive of the endpoints. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

We claim:

1. A system comprising:
   (a) a first neural network configured to:
      detect, from a first image of a first cross section of a body part and its surrounding body part, a first outer boundary of the first cross section of the body part and a first inner boundary of the first cross section of the body part, and
      detect, from a second image of a second cross section of the body part and the surrounding body part, a second outer boundary of the second cross section of the body part and a second inner boundary of the second cross section of the body part;
   (b) a model generator configured to:
      generate a three dimensional model of the body part by connecting points on the first outer boundary and the second outer boundary, and connecting points on the first inner boundary and the second inner boundary, wherein the three dimensional model comprises shape indices and location information of the shape indices;
   (c) a second neural network configured to:
      predict wall stress of the body part, according to the three dimensional model generated based on the first outer boundary, the first inner boundary, the second outer boundary, and the second inner boundary; and
   (d) a risk determinator configured to:
      compare, for each point of the three dimensional model, the wall stress to a threshold, and
      provide an indication associated with the three dimensional model indicative of a risk of rupture according to the wall stress exceeding the threshold.

2. The system of claim 1, wherein the model generator is coupled between the first neural network and the second neural network, and wherein the second neural network is configured to predict the wall stress of the body part according to geometry information comprising the three dimensional model derived from the first outer boundary, the first inner boundary, the second outer boundary, and the second inner boundary.

3. The system of claim 2, wherein the model generator is configured to:
   determine the shape indices from the generated three dimensional model, and
   provide the shape indices as input to the second neural network to predict the wall stress of the body part.

4. The system of claim 2, wherein the geometry information includes the shape indices and the location information of the shape indices.

5. The system of claim 4, wherein the shape indices include at least one of: a z-height ratio, a distance to a centroid, an intraluminal thrombus thickness, a principal curvature of a neighboring node, tortuosity, or a wall to lumen vector.

6. The system of claim 2, wherein in a training phase for the second neural network, the second neural network is configured to:
   predict the wall stress of the body part;
   compare the predicted wall stress with a target wall stress of the body part; and
   update a configuration of the second neural network according to the comparison.

7. The system of claim 1, wherein the body part has a tubular structure.

8. The system of claim 1, wherein the body part is an artery, the first outer boundary and the second outer boundary corresponding to a wall of the artery, and the first inner boundary and the second inner boundary corresponding to a lumen of the artery.

9. The system of claim 1, further comprising:
   a geometric information generator coupled between the first neural network and the second neural network, the geometric information generator configured to determine geometry information according to the first outer boundary, the first inner boundary, the second outer boundary, and the second inner boundary, the geometry information comprising the shape indices.

10. The system of claim 1, wherein the second neural network comprises a regression model.

11. The system of claim 1, wherein the first neural network comprises a convolutional neural network.

12. The system of claim 1, further comprising:
    a risk determiner configured to determine a risk of an aneurysm according to the predicted wall stress of the body part.

13. The system of claim 1, wherein during a training phase of the first neural network, the first neural network is configured to:
    receive, as part of training data, a plurality of images each comprising a corresponding cross section of the body part and the surrounding body part; and
    receive, as part of the training data, for each of the plurality of images, an outer boundary of the corresponding cross section of the body part, and an inner boundary of the corresponding cross section of the body part.

14. A method comprising:
    (a) detecting, by a first neural network, from a first image of a first cross section of a body part of a subject and its surrounding body part, a first outer boundary of the first cross section of the body part and a first inner boundary of the first cross section of the body part;
    (b) detecting, by the first neural network, from a second image of a second cross section of the body part and the surrounding body part, a second outer boundary of the second cross section of the body part and a second inner boundary of the second cross section of the body part;
    (c) generating, by a model generator, a three dimensional model of the body part by connecting points on the first outer boundary and the second outer boundary, and connecting points on the first inner boundary and the second inner boundary, wherein the three dimensional model comprises a plurality of shape indices and location information of the plurality of shape indices;
(d) predicting, by a second neural network, wall stress of the body part of the subject, according to the three dimensional model generated based on the first outer boundary, the first inner boundary, the second outer boundary, and the second inner boundary;
(e) comparing, by a risk determinator, for each point of the three dimensional model, the wall stress to a threshold; and
(f) providing, by the risk determinator, an indication associated with the three dimensional model indicative of a risk of rupture according to the wall stress exceeding the threshold.

15. The method of claim 14, further comprising:
evaluating a risk of an abdominal aortic aneurysm, a ventricular aneurysm, or a brain aneurysm, according to the predicted wall stress.

16. The method of claim 14, wherein the body part has a tubular structure.

17. The method of claim 14, wherein the body part is a human body part, the human body part including an aorta, artery, ureter, intestine, or heart.

18. A system comprising:
(a) a first neural network configured to:
detect, from a first image of a first cross section of a body part and its surrounding body part, a first outer boundary of the first cross section of the body part and a first inner boundary of the first cross section of the body part;
(b) a model generator configured to:
generate a three dimensional model of the body part by connecting points on the first outer boundary, and connecting points on the first inner boundary, wherein the three dimensional model comprises shape indices and location information of the shape indices;
(c) a second neural network configured to:
predict wall stress of the body part, according to the three dimensional model generated based on the first outer boundary and the first inner boundary; and
(d) a risk determinator configured to:
compare each point of the three dimensional model to a threshold, and
provide an indication of one or more points of the three dimensional model exceeding the threshold indicative of a risk of rupture.

19. The system of claim 18,
wherein the second neural network is configured to predict the wall stress of the body part according to geometry information including the shape indices and the location information of the shape indices, and
wherein the shape indices include at least one of: a z-height ratio, a distance to a centroid, an intraluminal thrombus thickness, a principal curvature of a neighboring node, tortuosity, or a wall to lumen vector.

* * * * *

UNITED STATES PATENT AND TRADEMARK OFFICE
CERTIFICATE OF CORRECTION

| | | |
|---|---|---|
| PATENT NO. | : 12,329,546 B2 | Page 1 of 1 |
| APPLICATION NO. | : 17/769327 | |
| DATED | : June 17, 2025 | |
| INVENTOR(S) | : Chung et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 582 days.

Signed and Sealed this
Thirtieth Day of September, 2025

John A. Squires
*Director of the United States Patent and Trademark Office*